(12) United States Patent
Huang

(10) Patent No.: US 9,675,652 B2
(45) Date of Patent: Jun. 13, 2017

(54) COMPOSITIONS AND METHODS TO RELIEVE CHRONIC DISEASES SYMPTOMS

(75) Inventor: Andy Teh-An Huang, Cupertino, CA (US)

(73) Assignee: HXLS Charity Corp., Cupertino, CA (US)

( * ) Notice: Subject to any disclaimer, the term of this patent is extended or adjusted under 35 U.S.C. 154(b) by 61 days.

(21) Appl. No.: 13/556,886

(22) Filed: Jul. 24, 2012

(65) Prior Publication Data

US 2013/0028968 A1     Jan. 31, 2013

Related U.S. Application Data

(60) Provisional application No. 61/513,494, filed on Jul. 29, 2011.

(51) Int. Cl.
```
A61K 36/06      (2006.01)
A61K 36/258     (2006.01)
A61K 36/28      (2006.01)
```
(52) U.S. Cl.
CPC .............. *A61K 36/06* (2013.01); *A61K 36/28* (2013.01)

(58) Field of Classification Search
None
See application file for complete search history.

(56) References Cited

U.S. PATENT DOCUMENTS

| | | |
|---|---|---|
| 7,456,225 B1 | 11/2008 | Liu et al. |
| 2003/0113297 A1 | 6/2003 | Chen et al. |
| 2005/0129780 A1 | 6/2005 | Holcomb-Halstead et al. |
| 2006/0110479 A1 | 5/2006 | Mitra et al. |
| 2007/0041993 A1 | 2/2007 | Holcomb-Halstead et al. |
| 2009/0118364 A1 | 5/2009 | Lai et al. |
| 2009/0130138 A1 | 5/2009 | Stamets |
| 2011/0052731 A1* | 3/2011 | Park et al. ................... 424/728 |
| 2012/0039928 A1* | 2/2012 | Park et al. ................ 424/195.15 |
| 2012/0177730 A1* | 7/2012 | Baron et al. .................. 424/452 |

FOREIGN PATENT DOCUMENTS

| | | |
|---|---|---|
| WO | WO 97/002831 A1 | 1/1997 |
| WO | WO 02/032444 A1 | 4/2002 |
| WO | WO 2006/015556 A1 | 2/2006 |

OTHER PUBLICATIONS

Way et al. (2010) J. Agric. Food Chem. 58, 3356-3365.*
Wang et al. (1997) Int. J. Cancer: 70, 699-705.*
Park et al. (2009) Journal of Ethnopharmacology 121: 304-312.*
Byambaragchaa, et al. (2013) Asian Pac. J. Cancer Prev. 14(9): 5397-5402.*
Lee et al. (2005) Mutagenesis vol. 20, No. 4, pp. 237-243.*
Yi et al. (2009) Chromatographia 69, pp. 537-542.*
Shuliang, H. (1995) Carcinogeneisis Turatogenesis and Mutagenesis, vol. 7, No. 2.*
Lu et al. (2003) Oncology Reports 10: 375-379.*
Mazzio, et al. (2009) Phytother. Res. 23, 385-398.*

* cited by examiner

*Primary Examiner* — Chris R Tate
*Assistant Examiner* — Russell Fiebig
(74) *Attorney, Agent, or Firm* — Finnegan, Henderson, Farabow, Garrett & Dunner, LLP

(57) ABSTRACT

Compounds having unique properties are prepared from the herbal compositions described herein and comprise extracts derived from plants and fungi of the genera *Panax*, *Ganoderma*, and *Saussurea*. The compositions are useful in preventing, treating, relieving, and improving the quality-of-life of patients suffering from chronic diseases, such as liver diseases, cancer, cachexia, and immune system disorders.

9 Claims, No Drawings

COMPOSITIONS AND METHODS TO RELIEVE CHRONIC DISEASES SYMPTOMS

I claim the benefit of Provisional Patent Application No. 61/513,494 filed on Jul. 29, 2011

TECHNICAL FIELD

This application pertains to compositions comprising a combination of extracts from plants of the genera *Panax, Ganoderma*, and *Saussurea* and methods for using the same to relieve the symptoms of chronic diseases in individuals.

BACKGROUND

Hepatitis is one of the most widespread chronic infections within the global population. Most commonly caused via infection by one of five viruses (hepatitis A, B, C, D, and E), hepatitis is defined by inflammation of the liver and characterized by the presence of inflammatory cells in liver tissue. According to the World Health Organization (WHO), the most serious type of viral hepatitis is Hepatitis B (HBV), a potentially life-threatening liver infection caused by the hepatitis B virus. Transmitted through contact with blood or other bodily fluids of an infected person, HBV is 50 to 100 times more infectious than Human Immunodeficiency Virus (HIV) and, unlike HIV, can survive outside of a host organism for up to 7 days. During that time, HBV retains the ability to cause infection if it comes into contact with a non-infected individual. WHO's fact sheet indicates that about 2 billion people worldwide have been infected with HBV and about 350 million more are living with chronic HBV infection (WHO Hepatitis Fact Sheet, August, 2008, www.who.int/mediacentre/factsheets/fs204/en/). While a vaccine against HBV has been available since 1982, there is currently no cure for those who are already infected. The 350 million people globally who are living with chronic HBV infection are highly susceptible to HBV-related liver cirrhosis, liver cancer, or death. WHO estimates 600,000 persons die each year due to acute or chronic consequences of HBV, and ranked liver cancer as the third leading cause of HBV-related death worldwide.

Cancer is a large, heterogeneous class of diseases in which a group of cells display uncontrolled growth and invasion that intrudes upon and destroys adjacent tissues. Cancer often metastasizes, spreading to other locations in the body via the lymphatic system or through the bloodstream. According to the American Cancer Society, cancer is the second leading cause of death in the U.S., with half of all men and one-third of all women developing some form of cancer during their lifetimes (Snowden, ACS Researchers: Progress, Challenges in the War on Cancer, 2010, www.cancer.org/Cancer/news/News/acs-researchers-progress-chal). WHO accounted for over 7.6 million deaths and 12.7 million incidents of cancer globally in 2008 and estimates 21 million new cases by 2030 with a mortality rate of 13 million deaths per year (WHO Cancer Fact Sheet, February, 2011, www.who.int/mediacentre/factsheets/fs297/en/).

There is no total and complete cure for chronic diseases such as HBV and cancer. While there are limited numbers of drugs developed to treat HBV, many suffer from one or more disadvantages, most notably adverse side-effects, build-up of viral resistance, complex administration methods, and often high cost. Similarly, cancer treatment methods, including chemotherapy, radiation therapy, and surgery often possess significant adverse side effects. These generally include removal of healthy tissue during surgery, death of non-cancerous cells during chemotherapy and radiation therapy, and significant reduction of white blood cells and other immune system components leading to increased susceptibility for infection. Moreover, the toxicity of many cancer treatments can cause the failure of organ systems, such as the liver and the kidney, as a complication of those treatments.

Therefore, there remains a need for simple and effective natural compositions that are well tolerated, simple to administer, and relatively inexpensive to relieve the symptoms of chronic diseases such as HBV and cancer. These natural compositions may be utilized in an adjuvant or neoadjuvant setting to ease suffering, to improve quality of life, and to relieve the symptoms of patients suffering from chronic diseases with reduced side effects.

Throughout this specification, various patents, patent applications and other types of publications (e.g., journal articles) are referenced. The disclosure of all patents, patent applications, and publications cited herein are hereby incorporated by reference in their entirety for all purposes.

BRIEF SUMMARY OF THE INVENTION

Provided herein are compositions and methods to relieve the symptoms of chronic diseases in individuals. The compositions comprise a combination of herbal extracts derived from plants and fungi of the genera *Panax, Ganoderma*, and *Saussurea*. The compositions provided herein can be administered to individuals suffering from chronic diseases for relief of symptoms associated with those diseases.

Accordingly, provided herein are compositions comprising an extract derived from a plant of the genus *Panax*, an extract derived from a fungus of the genus *Ganoderma*, and an extract derived from a plant from the genus *Saussurea*.

Also provided herein are methods for treating a chronic disease in an individual comprising administering to the individual an effective amount of the compositions disclosed herein.

DETAILED DESCRIPTION OF THE INVENTION

Plants and fungi from the genera *Panax, Ganoderma*, and *Saussurea* have been used as herbs in Traditional Chinese Medicine (TCM) for thousands of years. The herbs, as derived from their original Chinese names, are known as Baishen, Lingzhi, and Snow-Lotus-Flower, respectively. Baishen, referring to plants of the genus *Panax*, also known as Ginseng, is a commonly used herbal medicine and is reported to promote the central nervous system, cardiovascular system, and immune system. Lingzhi, a fungus of the genus *Ganoderma*, has been used in traditional Chinese medicine for more than four thousand years. The most well-known pharmacological functions of Lingzhi are anti-tumor and immunomodulatory activities. Snow-Lotus-Flower, referring to plants of the genus *Saussureae*, is a precious and rare herb in traditional Chinese medicine and has been documented as possessing anti-cancer, anti-inflammatory, and anti-arthritis activities.

The compositions and methods disclosed herein provide a pharmacological use of extracts derived from each of these plants and fungi together. An extract derived from a combination of plants and fungi from the genera *Panax, Ganoderma*, and *Saussurea* (the "extract") may be useful in treating chronic human diseases, including inhibition of HBV antigen expression, inhibition of inflammatory cytokine secretion, inhibition of human cancer cell proliferation, inhibition of liver damage, inhibition of hepatoma formation, and prevention of cachexia.

General Techniques

The practice of the present invention will employ, unless otherwise indicated, conventional techniques of molecular biology, microbiology, cell biology, biochemistry, nucleic acid chemistry, and immunology, which are well known to those skilled in the art. Such techniques are explained fully in the literature, such as, *Molecular Cloning: A Laboratory Manual*, second edition (Sambrook et al., 1989) and *Molecular Cloning: A Laboratory Manual*, third edition (Sambrook and Russel, 2001), (jointly referred to herein as "Sambrook"); *Current Protocols in Molecular Biology* (F. M. Ausubel et al., eds., 1987, including supplements through 2001); *PCR: The Polymerase Chain Reaction*, (Mullis et al., eds., 1994); Harlow and Lane (1988) *Antibodies, A Laboratory Manual*, Cold Spring Harbor Publications, New York; Harlow and Lane (1999) *Using Antibodies: A Laboratory Manual* Cold Spring Harbor Laboratory Press, Cold Spring Harbor, N.Y. (jointly referred to herein as "Harlow and Lane"), Beaucage et al. eds., *Current Protocols in Nucleic Acid Chemistry* John Wiley & Sons, Inc., New York, 2000), and *Handbook of Experimental Immunology*, 4th edition (D. M. Weir & C. C. Blackwell, eds., Blackwell Science Inc., 1987).

DEFINITIONS

As used herein, the singular form "a", "an", and "the" includes plural references unless indicated otherwise.

An "individual" is a mammal including a human. Mammals include, but are not limited to, farm animals, sport animals, pets, non-human primates, mice and rats. Individuals also include companion animals including, but not limited to, dogs and cats. In one aspect, an individual is a human. In another aspect, an individual is a rodent.

A "plant" broadly encompasses monocots, dicots, and associated microorganisms belonging to the kingdom Plantae. Plants include, without limitation organisms such as trees, flowers, herbs, bushes, grasses, vines, ferns, mosses, and green algae.

As used herein, the term "fungus" refers to a large group of eukaryotic organisms that includes, without limitation, microorganisms such as yeasts and molds as well as mushrooms and toadstools.

As used herein, the term "extract" refers to plant or fungus extracts that may be prepared by liquid or powder extraction or any other method known to one having skill in the art and may or may not include a step of concentrating the extract as well as further processing (for example, but not limited to, drying and/or refluxing). The extractions disclosed herein may be obtained from any part of a plant or fungus (for example, but not limited to, roots, leaves, flowers, seeds, stems, stalks, caps, or spores) as well as whole plants and fungi.

As used herein, "treatment" or "treating" is an approach for obtaining beneficial or desired results including clinical results. Beneficial or desired clinical results can include, but are not limited to, one or more of the following: decreasing symptoms resulting from the disease, increasing the quality of life of those suffering from the disease, decreasing the dose of other medications required to treat the disease, delaying the progression of the disease, and/or prolonging survival of individuals.

As used herein, "delaying development of a disease" means to defer, hinder, slow, retard, stabilize, and/or postpone development of the disease (such as cancer) or symptoms of the disease. This delay can be of varying lengths of time, depending on the history of the disease and/or individual being treated. As is evident to one skilled in the art, a sufficient or significant delay can, in effect, encompass prevention, in that the individual does not develop the disease.

As used herein, an "effective dosage" or "effective amount" of drug, compound, or pharmaceutical composition is an amount sufficient to effect beneficial or desired results. For prophylactic use, beneficial or desired results can include, for example, one or more results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results can include, for example one or more clinical results such as decreasing one or more symptoms and pathological conditions resulting from or associated with the disease, increasing the quality of life of those suffering from the disease, decreasing the dose of other medications required to treat the disease, enhancing effect of another medication such as via targeting, delaying the progression of the disease, and/or prolonging survival. An effective dosage can be administered in one or more administrations. An effective dosage of drug, compound, or pharmaceutical composition can be, for example, an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Compositions of the Invention

In some aspects, provided herein are herbal compositions comprising an extract derived from a plant of the genus *Panax*, an extract derived from a fungus of the genus *Ganoderma*, and an extract derived from a plant from the genus *Saussurea*. The herbal compositions are derived from extracts of at least one plant and fungus from each of the three genera. In some embodiments, the composition can be derived from extracts from at least one plant of the genus *Panax*, extracts from at least one fungus from the genus *Ganoderma*, and extracts from at least one plant from the genus *Saussurea*. In another embodiment, the composition can be derived from extracts from one plant of the genus *Panax*, extracts from one fungus from the genus *Ganoderma*, and extracts from one plant from the genus *Saussurea*. In some embodiments, the compositions can be derived from extracts of more than one plant or fungi within each genera. In some embodiments, the composition can be derived from any of 3, 4, 5, 6, 7, 8, 9, 10, 11, 12, 13, 14, or 15 total plants and fungi from the genera *Panax, Ganoderma*, and *Saussurea*. The compositions disclosed herein can be prepared from the extracts of any part of the plants and fungi, including, but not limited to, portions of plants and fungi (for example, roots, leaves, flowers, seeds, stems, stalks, caps, or spores) and whole plants and fungi.

*Panax*

Ginseng is a broad name given to any one of eleven distinct species of slow-growing perennial plants with fleshy roots, belonging to the *Panax* genus in the family Araliaceae. Ginseng grows mainly in the Northern Hemisphere and is found in eastern Asia (mostly Korea, the Manchuria region of northern China, and eastern Siberia) and North America (in the Canadian provinces of Ontario and British Columbia as well as the American state of Wisconsin), typically in cooler climates. *Panax vietnamensis*, which grows in Vietnam, is the southernmost natural ginseng identified. Ginseng produces ginsenosides, which are a class of steroid glycosides and triterpene saponins found exclusively in plants of the genus *Panax* and which are thought to be the source of many of ginseng's medicinal properties.

The compositions disclosed herein contain extracts of at least one plant of the genus *Panax*. Plants of the genus *Panax* can include, without limitation, *Panax ginseng, Panax quinquefolia, Panax bipinnatifidus, Panax japonicus, Panax quinquefolius, Panax vietnamensis, Panax wangianus, Panax zingiberensis, Panax stipuleanatus*, or *Panax notoginseng*. In some embodiments, the compositions disclosed herein can contain extracts of any of 1, 2, 3, 4, 5, 6, 7, 8, 9, or 10 plants of the genus *Panax*.

Additionally, the compositions disclosed herein can also contain extracts derived from one or more ginseng alternatives. As used herein, a "ginseng alternative" refers to mostly adaptogenic plants which are sometimes commonly referred to as ginsengs, but that are from a different family or genus (i.e. are not members of the genus *Panax*). Ginseng alternatives can include, without limitation, *Gynostemma pentaphyllum, Eleutherococcus senticosus, Pseudostellaria heterophylla, Withania somnifera, Pfaffia paniculata, Lepidium meyenii, Oplopanax horridus*, and *Angelica sinensis*. In some embodiments, the compositions disclosed herein can contain extracts of any of 1, 2, 3, 4, 5, 6, 7, 8, 9, or 10 ginseng alternatives.

In some aspects, the compositions provided herein can comprise extracts from one or more plant of the genus *Panax*, extracts from at least one fungus of the genus *Ganoderma*, and extracts from at least one plant from the genus *Saussurea*. In one embodiment, the compositions provided herein can comprise extracts from two plants of the genus *Panax*, extracts from at least one fungus of the genus *Ganoderma*, and extracts from at least one plant from the genus *Saussurea*. In one embodiment, the compositions provided herein can comprise extracts from three plants of the genus *Panax*, extracts from at least one fungus of the genus *Ganoderma*, and extracts from at least one plant from the genus *Saussurea*. In one embodiment, the compositions provided herein can comprise extracts from four plants of the genus *Panax*, extracts from at least one fungus of the genus *Ganoderma*, and extracts from at least one plant from the genus *Saussurea*. In one embodiment, the compositions provided herein can comprise extracts from five plants of the genus *Panax*, extracts from at least one fungus of the genus *Ganoderma*, and extracts from at least one plant from the genus *Saussurea*. In one embodiment, the compositions provided herein can comprise extracts from six plants of the genus *Panax*, extracts from at least one fungus of the genus *Ganoderma*, and extracts from at least one plant from the genus *Saussurea*. In one embodiment, the compositions provided herein can comprise extracts from seven plants of the genus *Panax*, extracts from at least one fungus of the genus *Ganoderma*, and extracts from at least one plant from the genus *Saussurea*. In one embodiment, the compositions provided herein can comprise extracts from eight plants of the genus *Panax*, extracts from at least one fungus of the genus *Ganoderma*, and extracts from at least one plant from the genus *Saussurea*. In one embodiment, the compositions provided herein can comprise extracts from nine plants of the genus *Panax*, extracts from at least one fungus of the genus *Ganoderma*, and extracts from at least one plant from the genus *Saussurea*. In one embodiment, the compositions provided herein can comprise extracts from ten plants of the genus *Panax*, extracts from at least one fungus of the genus *Ganoderma*, and extracts from at least one plant from the genus *Saussurea*.

In some aspects, the compositions provided herein can comprise extracts from one or more plants of the genus *Panax* and/or extracts from one or more ginseng alternatives, extracts from at least one fungus of the genus *Ganoderma*, and extracts from at least one plant from the genus *Saussurea*. In one embodiment, the compositions provided herein can comprise extracts from any of 1, 2, 3, 4, 5, 6, 7, 8, 9, or 10 plant(s) of the genus *Panax* and/or extracts from one or more ginseng alternatives, extracts from at least one fungus of the genus *Ganoderma*, and extracts from at least one plant from the genus *Saussurea*. In another embodiment, the compositions provided herein can comprise extracts from one or more plants of the genus *Panax* and/or extracts from any of 1, 2, 3, 4, 5, 6, 7, 8, 9, or 10 ginseng alternatives, extracts from at least one fungus of the genus *Ganoderma*, and extracts from at least one plant from the genus *Saussurea*.

*Ganoderma*

*Ganoderma* is a genus of polypore mushrooms which grow on wood and include about 80 species, many from tropical regions. Differentiated from other polypores due to their double walled basidiospore, species of this genus are generally known as "shelf mushrooms" or "bracket mushrooms." *Ganoderma* are characterized by basidiocarps that are large, perennial, and possessing woody brackets, also known as "conks" These fungi are lignicolous, leathery, and may grow either with or without a stem. The fruit bodies of *Ganoderma* species typically grow in a fanlike or hooflike form on the trunks of living or dead trees and produce double-walled, truncate spores.

The compositions disclosed herein contain extracts of at least one fungus of the genus *Ganoderma*. Fungi of the genus *Ganoderma* can include, without limitation *Ganoderma lucidum, Ganoderma tsugae*, or *Ganoderma camphoratum*. In some embodiments, the compositions disclosed herein can contain extracts of any of 1, 2, or 3 fungi of the genus *Ganoderma*.

Additionally, the compositions disclosed herein can also contain extracts derived from one or more *Ganoderma* alternatives. As used herein, "*Ganoderma* alternative" refers to other fungi known to have medicinal properties in traditional Chinese medicine. In some embodiments, *Ganoderma* alternatives are fungi of the genus *Antrodia*. Examples of *Ganoderma* alternatives can include, without limitation, *Antrodia cinnamomea, Antrodia camphorate, Antrodia salmonea*, or *Taiwanofungus camphorates*. In some embodiments, the compositions disclosed herein can contain extracts of any of 1, 2, 3, or 4 *Ganoderma* alternatives.

In some aspects, the compositions provided herein can comprise extracts from at least one plant of the genus *Panax*, extracts from one or more fungus of the genus *Ganoderma*, and extracts from at least one plant from the genus *Saussurea*. In one embodiment, the compositions provided herein can comprise extracts from at least one plant of the genus *Panax*, extracts from at least two fungi of the genus *Ganoderma*, and extracts from at least one plant from the genus *Saussurea*. In one embodiment, the compositions provided herein can comprise extracts from at least one plant of the genus *Panax*, extracts from at least three fungi of the genus *Ganoderma*, and at least one plant from the genus *Saussurea*.

In some aspects, the compositions provided herein can comprise extracts from at least one plant of the genus *Panax* and/or extracts from one or more ginseng alternatives, extracts from one or more fungi of the genus *Ganoderma* and/or extracts from one or more *Ganoderma* alternatives, and extracts from at least one plant from the genus *Saussurea*. In one embodiment, the compositions provided herein can comprise extracts from at least one plant of the genus *Panax* and/or extracts from one or more ginseng alternatives, extracts from any of 1, 2, or 3 fungi of the genus *Ganoderma* and/or extracts from one or more *Ganoderma* alternatives, and extracts from at least one plant from the genus *Saussurea*. In another embodiment, the compositions provided herein can comprise extracts from at least one plant of the genus *Panax*, extracts from one or more fungi of the genus *Ganoderma* and/or extracts from any of 1, 2, 3, or 4 *Ganoderma* alternatives, and extracts from at least one plant from the genus *Saussurea*.

Saussurea

*Saussurea* is a genus of about 300 species of flowering plants in the family Asteraceae, which are native to cool temperate and arctic regions of Asia, Europe, and North America, with the highest diversity in alpine habitats in the Himalaya and central Asia. Common names include "sawwort" and "snow lotus," the latter used for a number of high altitude species in central Asia. Plants of *Saussurea* are perennial herbaceous plants, ranging in height from dwarf alpine species (5-10 cm tall), to tall thistle-like plants (up to 3 m tall). The leaves are produced in a dense basal rosette, and then spirally up the flowering stem. The flowers form in a dense head of small capitula, often completely surrounded in dense white to purple woolly hairs and the individual florets are white to purple.

The compositions disclosed herein contain extracts of at least one plant of the genus *Saussurea*. Plants of the genus *Saussurea* can include, without limitation, *Saussurea involucrata*, *Saussurea lappa*, *Saussurea auriculata*, *Saussurea alpina*, *Saussurea chinnampoensis*, *Saussurea controversa*, *Saussurea americana*, *Saussurea angustifolia*, *Saussurea amara*, *Saussurea angustifolia*, *Saussurea auriculata*, *Saussurea bhutkesh*, *Saussurea cana*, *Saussurea ceratocarpa*, *Saussurea deltoidea*, *Saussurea densa*, *Saussurea dhwojii*, *Saussurea discolor*, *Saussurea formosana*, *Saussurea glandulosa*, *Saussurea kanzanensis*, *Saussurea kiraisanensis*, *Saussurea medusa*, *Saussurea salsa*, *Saussurea manshurica*, *Saussurea mongolica*, *Saussurea nepalensis*, *Saussurea obvallata*, *Saussurea pulchella*, *Saussurea pygmaea*, *Saussurea ussuriensis*, *Saussurea veitchiana*, *Saussurea obvallata*, *Saussurea hieracioides*, *Saussurea laniceps*, *Saussurea costus*, *Saussurea elegans*, and *Saussurea gnaphalodes*. In some embodiments, the compositions disclosed herein can contain extracts of any of 1, 2, 3, 4, 5, 6, 7, 8, 9, 10, 11, 12, 13, 14, 15, 16, 17, 18, 19, 20, about 25, about 30, or about 35 plants of the genus *Saussurea*, inclusive, including any number in between these values.

In some aspects, the compositions provided herein can comprise extracts from at least one plant of the genus *Panax*, extracts from at least one fungus of the genus *Ganoderma*, and extracts from one or more plant from the genus *Saussurea*. In one embodiment, the compositions provided herein can comprise extracts from at least one plant of the genus *Panax*, extracts from at least one fungus of the genus *Ganoderma*, and extracts from two plants from the genus *Saussurea*. In one embodiment, the compositions provided herein can comprise extracts from at least one plant of the genus *Panax*, extracts from at least one fungus of the genus *Ganoderma*, and extracts from three plants from the genus *Saussurea*. In one embodiment, the compositions provided herein can comprise extracts from at least one plant of the genus *Panax*, extracts from at least one fungus of the genus *Ganoderma*, and extracts from four plants from the genus *Saussurea*. In one embodiment, the compositions provided herein can comprise extracts from at least one plant of the genus *Panax*, extracts from at least one fungus of the genus *Ganoderma*, and extracts from five plants from the genus *Saussurea*. In one embodiment, the compositions provided herein can comprise extracts from at least one plant of the genus *Panax*, extracts from at least one fungus of the genus *Ganoderma*, and extracts from six plants from the genus *Saussurea*. In one embodiment, the compositions provided herein can comprise extracts from at least one plant of the genus *Panax*, extracts from at least one fungus of the genus *Ganoderma*, and extracts from seven plants from the genus *Saussurea*. In one embodiment, the compositions provided herein can comprise extracts from at least one plant of the genus *Panax*, extracts from at least one fungus of the genus *Ganoderma*, and extracts from at least eight plants from the genus *Saussurea*. In one embodiment, the compositions provided herein can comprise extracts from at least one plant of the genus *Panax*, extracts from at least one fungus of the genus *Ganoderma*, and extracts from nine plants from the genus *Saussurea*. In one embodiment, the compositions provided herein can comprise extracts from at least one plant of the genus *Panax*, extracts from at least one fungus of the genus *Ganoderma*, and extracts from ten plants from the genus *Saussurea*. In one embodiment, the compositions provided herein can comprise extracts from at least one plant of the genus *Panax*, extracts from at least one fungus of the genus *Ganoderma*, and extracts from any of about 12, about 15, about 20, about 25, about 30, about 35, or about 38 plants from the genus *Saussurea*, inclusive, including any number in between these values.

In some aspects, the compositions provided herein can comprise extracts from one or more plants of the genus *Panax* and/or extracts from one or more ginseng alternatives, extracts from one or more fungi of the genus *Ganoderma* and/or extracts from one or more *Ganoderma* alternatives, and extracts from one or more plant from the genus *Saussurea*. In one embodiment, the compositions provided herein can comprise extracts from any of 1, 2, 3, 4, 5, 6, 7, 8, 9, or 10 plant(s) of the genus *Panax* and/or extracts from any of 1, 2, 3, 4, 5, 6, 7, 8, 9, or 10 ginseng alternatives, extracts from any of 1, 2, or 3 fungi of the genus *Ganoderma* and/or extracts from any of 1, 2, 3, or 4 *Ganoderma* alternatives, and extracts from any of about 1, 2, 3, 4, 5, 6, 7, 8, 9, or 10, about 12, about 15, about 20, about 25, about 30, about 35, or about 38 plants from the genus *Saussurea*, inclusive, including any number in between these values.

Pharmaceutical Excipients

Addition of other materials to the compositions described herein can be desirable. Other inactive material or combination of materials that are suitable for administration, "excipients", can be added to the compositions described herein. Frequently, excipients serve to improve the features of the therapeutic agent composition, e.g., by providing more efficient and reproducible delivery of the therapeutic agent, improving the handling characteristics of powders (e.g., flowability and consistency), the stability of the agent, and/or facilitating manufacturing and filling of dosage forms. In particular, excipient materials may function to further improve the physical and chemical stability of the therapeutic agent, and enhance uptake of the therapeutic agent into body, thus increasing efficacy of the therapeutic agent. Excipients may further serve to minimize the residual moisture content and/or hinder moisture uptake, minimize particle aggregation, or modify particle surface properties (i.e., rugosity) of the compositions. An excipient may also serve as a bulking agent when it is desired to reduce the concentration of therapeutic agent in the formulation. Furthermore, an excipient may server as a masking agent for objectionable smells and/or tastes.

Useful excipients that may be added to the compositions described herein include, but are not limited to, fluidizers, lubricants, adhesion agents, surfactants, acidifying agents, alkalizing agents, agents to adjust pH, antimicrobial preservatives, antioxidants, anti-static agents, buffering agents, chelating agents, humectants, gel-forming agents, or wetting agents. Excipients also include coloring agents, coating agents, sweetening, flavoring and perfuming and other masking agents. The compositions and formulations of this invention may include a therapeutic agent with an individual excipient or with multiple excipients in any suitable combination, with or without a carrier.

In some embodiments of the invention, a water-absorbing and gel-forming material is added to the composition to improve drug absorption. Typically, this gel-forming material is used as a carrier, either alone or in combination with a water-absorbing, but non-gel-forming substance. Exemplary, gel-forming materials include, for example, cellulose derivatives such as hydroxypropyl cellulose, hydroxypropyl methyl cellulose, methyl cellulose, hydroxy ethyl cellulose, and carboxymethyl cellulose sodium.

Representative examples of wetting agents include, for example, gelatin, casein, lecithin (phosphatides), gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., TWEEN™), polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxy propylcellulose, hydroxypropylmethylcellulose phthlate, noncrystalline cellulose, magnesium aluminum silicate, triethanolamine, polyvinyl alcohol, and polyvinylpyrrolidone (PVP).

Useful sweetening agents include, for example, D-sorbitol, glycyrrhizia, saccharin, and stevia.

It should be appreciated that there may be considerable overlap in function of excipients used in the compositions described herein. Thus, the categorization of the above-listed excipients should be taken as merely exemplary, and not limiting, of the types of excipients that are contemplated for inclusions in the compositions and formulations described herein. Further examples of pharmaceutical excipients and/or additives of the above categories suitable for use in the compositions of the invention can be found in the *U.S. Pharmacopeia National Formulary*, 1990, pp. 1857-1859, as well as in Rowe, et al., *Handbook of Pharmaceutical Excipients*, 5th ed., 2006, and "*Remington: The Science and Practice of Pharmacy,*" 21st ed., 2006, editor David B. Troy, and in the *Physician's Desk Reference*, 52nd ed., Medical Economics, Monfvale, N.J., 1998, the contents of which are hereby incorporated by reference in their entirety.

Methods for Manufacturing the Compositions of the Invention

In some aspects, raw materials from plants and fungi from the genera *Panax, Ganoderma*, and *Saussurea* can be used to manufacture the compositions described herein. As used herein, "raw materials" means any part of a plant or fungus (for example, but not limited to, roots, leaves, flowers, seeds, stems, stalks, caps, or spores) as well as whole plants and fungi that can be used to make the compositions disclosed herein. In one embodiment, any of about 5, 6, 7, 8, 9, 10, 11, 12, 13, 14, 15, 16, 17, 18, 19, 20, 25, 30, 35, 40, 45, 50, 55, 60, 65, 70, 80, 90, 100, 200, 300, 400, 500, 600, 700, 800, 900, 1000, 2000, 3000, 4000, 5000, 6000, 7000, 8000, 9000, or 10000 g or more of raw materials, inclusive, including any value in between these numbers, from *Panax, Ganoderma*, and *Saussurea* can be used to make the compositions disclosed herein. The extracts can be obtained by extracting raw materials from *Panax, Ganoderma*, and *Saussurea* together or individually. Following extraction, the individually extracted material from *Panax, Ganoderma*, and *Saussurea* can be combined. In one embodiment, a liquid extract can be filtered away from the remaining solid material prior to being concentrated or, in the case of individual extractions, prior to being combined. In other embodiments, the remaining solid material can undergo further extraction. In some embodiments, the extracts can be concentrated or, alternatively, the extracts can be left in their raw unconcentrated form.

In some aspects, equal amounts of raw materials from plants and fungi from the genera *Panax, Ganoderma*, and *Saussurea* can be used to manufacture the compositions disclosed hereine. In other embodiments, the ratio of the raw materials from plants and fungi from the genera *Panax, Ganoderma*, and *Saussurea* can vary with respect to one another. Any ratio of raw material ingredients derived from *Panax, Ganoderma*, and *Saussurea* are contemplated for use in manufacturing the compositions disclosed herein. For example, in some embodiments, the ratio of raw materials of *Panax* compared to *Ganoderma*, and *Saussurea* can range from about 1:1:1, about 2:1:1, about 3:1:1, about 4:1:1, or about 5:1:1 respectively, including any amounts in between these ratios. In other embodiments, the ratio of raw materials of *Ganoderma* compared to *Panax* and *Saussurea* can range from about 1:1:1, about 2:1:1, about 3:1:1, about 4:1:1, or about 5:1:1 respectively, including any amounts in between these ratios. In other embodiments, the ratio of raw materials of *Saussurea* compared to *Ganoderma* and *Panax* can range from about 1:1:1, about 2:1:1, about 3:1:1, about 4:1:1, or about 5:1:1 respectively, including any amounts in between these ratios. In other embodiments, the ratios of any of the raw materials from *Panax, Ganoderma*, and *Saussurea* can vary in ratios of about 2:2:1, about 2:3:1, about 2:4:1, about 2:5:1, about 2:1:2, about 2:1:3, about 2:1:4, about 2:1:5, about 3:1:2, about 3:1:3, about 3:1:4, about 3:1:5, about 3:2:1, about 3:3:1, about 3:4:1, about 3:5:1, about 4:2:1, about 4:3:1, about 4:5:1, about 4:1:4, about 4:1:5, about 5:5:1, or about 5:1:5, including any value in between these ratios for all three ingredients.

In some aspects, the extracts are obtained by soaking raw materials from plants and fungi from the genera *Panax, Ganoderma*, and *Saussurea* in a liquid. The liquid can be, without limitation, deionized water or ethanol. In some embodiments, the ethanol can have a concentration of about 5%, 10%, 15%, 20%, 25%, 30%, 35%, 40%, 45%, 50%, 55%, 60%, 65%, 70%, 75%, 80%, 85%, 90%, 95%, or 100%, inclusive, including any value between these percentages. The raw materials can be soaked at room temperature during the extraction process or can be soaked in a liquid that has been heated. In some embodiments, the liquid can be heated to about 30° C., 35° C., 40° C., 45° C., 50° C., 55° C., 60° C., 65° C., 70° C., 75° C., 80° C., 85° C., 90° C., 95° C., or 100° C., inclusive, including any temperature in between these values. The raw materials can be soaked for any of about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 36 hours, about 48 hours, about 60 hours, about 72 hours, about 84 hours, about 96 hours, about 5 days, about 6 days, or about 7 days, inclusive, including any time period in between these values.

In some aspects, the extracts isolated from *Panax, Ganoderma*, and *Saussurea* are refluxed either before or after they are concentrated. As used herein, the term "reflux" refers to the portion of the overhead liquid product from a distillation column or fractionator that is returned to the upper part of the column during a laboratory or industrial distillation. The extracts can be refluxed either individually or in combination with each other. The extracts can be refluxed after being concentrated or without first being concentrated. Additionally, solid material from a prior extraction may be refluxed to obtain additional extracts from the left over solid material. In some embodiments, the solid material remaining from a previous water or ethanol extraction can be refluxed in the presence of additional water or ethanol. The extracts isolated from *Panax, Ganoderma*, and *Saussurea* or the solid material remaining from a previous extraction can be refluxed for about 30, 60, 90, 120, 150, 180, 210, 240, 270, 300, 330, 360, 390, 410, 440, 470, or 500 minutes, inclusive, including any times in between these values.

In some aspects the composition can be made by soaking the raw materials from *Panax, Ganoderma*, and *Saussurea* together in 40% ethanol at a temperature of 60° C. In another aspect, the composition can be made by soaking the raw materials from *Panax, Ganoderma*, and *Saussurea* together in 95% ethanol at a temperature of 60° C. In another aspect, the composition can be made by soaking the raw materials from *Panax, Ganoderma*, and *Saussurea* together in 95% ethanol and then refluxing the extract for 2 hours. In another aspect, the composition can be made by soaking the raw materials from *Panax, Ganoderma*, and/or *Saussurea* in deionized water at room temperature and then refluxing the extract(s) for 2 hours. In another aspect, the composition can be made by soaking the raw materials from *Panax, Ganoderma*, and *Saussurea* in deionized water individually, then combining the extracts, and then refluxing the combined extracts for 2 hours. In another aspect, the composition can be made by soaking the raw materials from *Panax, Ganoderma*, and/or *Saussurea* in 40% ethanol and then refluxing the extract(s) for 2 hours. In another aspect, the composition can be made by soaking the raw materials from *Panax, Ganoderma*, and *Saussurea* in 95% ethanol individually, then combining the extracts, and then refluxing the combined extracts for 2 hours.

The extracts comprising the compositions described herein, carriers, excipients, and other components may require grinding, milling, spray drying, or some other processing step before use. Frequently, the required processing converts the therapeutic agents into particles with a desired median size and/or a defined particle size distribution ranges. In some embodiments, the native or processed therapeutic extracts, carriers, excipients, and other components are suitable for use as is. In other embodiments, these ingredients require further processing, such as sieving, to achieve the desired or necessary particle size distributions.

Methods of Treatment Using the Compositions of the Invention

The compositions disclosed herein can be used for the treatment of chronic diseases in an individual. In some aspects, the method can comprise treating a chronic disease in an individual by administering to the individual an effective amount of any of the compositions disclosed herein. In some embodiments, the individual can be suffering from a chronic disease of the liver. In other embodiments, the individual can be diagnosed with or can be suspected of having cancer. In another embodiment, the individual can be suffering from an inflammatory disease or immune system disorder. In yet another embodiment, the individual can be experiencing cachexia due to a chronic disease.

Chronic Diseases of the Liver

Chronic liver diseases (such as chronic hepatitis, cirrhosis, and liver cancer) have been a major cause of deaths in humans for centuries. Liver diseases include viral liver disease, alcoholic liver disease, drug or toxicant-caused liver disease and metabolism disorder liver disease. In the world, about 350 million people are chronic B type hepatitis carriers, and 2.7 million people are chronic C type hepatitis carriers. In Taiwan, the B type hepatitis carrier rate is about 15 to 20% of the population and the C type hepatitis carrier 2Q rate is about 2 to 4% of the population.

One aspect of the invention provides for methods of using the compositions described herein to treat individuals who have been diagnosed with chronic diseases of the liver or are suspected of having chronic diseases affecting the liver. Common diseases affecting the liver include, but are not limited to, autoimmune hepatitis, hepatitis A, hepatitis B, hepatitis C, hepatitis D, hepatitis E, alcoholic cirrhosis of the liver, liver damage due to overdose of drugs or other toxins, liver damage due to ingestion of poisonous mushrooms, *Toxoplasma* infection, Hepatosplenic schistosomiasis, liver disease in syphilis, Epstein-Barr virus infection, yellow fever virus infection, rubella virus infection, leptospirosis, echinococcosis, amoebiasis, Reye's syndrome, and end stage liver disease.

In some aspects, any of the methods of treatment described herein can further comprise administering one or more additional liver-protecting therapies to the individual. These can include, without limitation, medicines for treating hepatitis, such as liver protecting drugs, and antiviral drugs or immune regulators. For example, interferon and lamivudine are commonly used for treating B type hepatitis.

Provided herein are methods of treating an individual suffering chronic disease of the liver comprising administering to the individual the herbal compositions provided herein. The individual can be administered an herbal composition comprising an extract derived from a plant of the genus *Panax*, an extract derived from a fungus of the genus

*Ganoderma*, and an extract derived from a plant from the genus *Saussurea*. Alternatively, the individual can be administered a composition comprising an active ingredient consisting essentially of an extract derived from a plant of the genus *Panax*, an extract derived from a fungus of the genus *Ganoderma*, and an extract derived from a plant of the genus *Saussurea*. The composition can be in a dosage form of a solution, a suspension, a liquid, a powder, a granule, an injection, a tablet, a capsule, or a pill. The composition can be administered in an adjuvant setting or administered in a neoadjuvant setting. The methods provided herein can further comprise administering one or more additional liver-protecting therapies to the individual. The compositions can additionally include one or more pharmaceutical excipients. In some embodiments, the composition used to treat chronic diseases of the liver can be a concentrated combined extract derived from 15 g of a plant of the genus *Panax*, 15 g of an extract derived from a fungus of the genus *Ganoderma*, and 15 g of an extract derived from a plant from the genus *Saussurea* which have been soaked in D.I. water at ambient temperature for 24 hours, filtered, and then the solid material refluxed in D.I. water for 2 hours. In some embodiments, the composition used to treat chronic diseases of the liver can be a concentrated combined extract derived from 15 g of a plant of the genus *Panax*, 15 g of an extract derived from a fungus of the genus *Ganoderma*, and 15 g of an extract derived from a plant from the genus *Saussurea* which have been extracted in D.I. water with reflux for 2 hours.

Cancer

One aspect of the invention provides for methods of using the compositions described herein to treat individuals who have been diagnosed with cancer or are suspected of having cancer. Common cancers contemplated include, but are not limited to, liver cancer, lung cancer, stomach cancer, cervical cancer, colorectal cancer, bone cancer, hemangiosarcoma, other sarcomas, breast cancer, testicular cancer, mast cell cancer, nasosinal cancer, bladder cancer, head and neck cancer, prostate cancer, brain cancer (including gliomas), soft-tissue carcinoma as well as all cancers of the blood (such as, but not limited to, leukemias and lymphomas). Also contemplated are those cancers that metastasize away from sites of primary tumor development via the blood and lymphatic systems.

The methods of the invention may be practiced in an adjuvant setting. "Adjuvant setting" refers to a clinical setting in which an individual has had a history of a proliferative disease, particularly cancer, and generally (but not necessarily) has been responsive to therapy, which includes, but is not limited to, surgery, radiotherapy, and chemotherapy. However, because of a history of the proliferative disease (such as cancer), these individuals are considered at risk of developing that disease. Treatment or administration in the "adjuvant setting" refers to a subsequent mode of treatment.

The methods provided herein may also be practiced in a "neoadjuvant setting," that is, the method may be carried out before the primary/definitive therapy. In some aspects, the individual has previously been treated. In other aspects, the individual has not previously been treated. In some aspects, the treatment is a first line therapy.

In some aspects, any of the methods of treatment described herein can further comprise administering one or more additional anti-cancer therapies to the individual. Various classes of anti-cancer agents can be used. Non-limiting examples include: alkylating agents, antimetabolites, anthracyclines, plant alkaloids, topoisomerase inhibitors, podophyllotoxin, antibodies (e.g., monoclonal or polyclonal), tyrosine kinase inhibitors (e.g., imatinib mesylate (Gleevec® or Glivec®)), hormone treatments, soluble receptors and other antineoplastics.

Topoisomerase inhibitors are also another class of anti-cancer agents that can be used. Topoisomerases are essential enzymes that maintain the topology of DNA Inhibition of type I or type II topoisomerases interferes with both transcription and replication of DNA by upsetting proper DNA supercoiling. Some type I topoisomerase inhibitors include camptothecins: irinotecan and topotecan. Examples of type II inhibitors include amsacrine, etoposide, etoposide phosphate, and teniposide. These are semisynthetic derivatives of epipodophyllotoxins, alkaloids naturally occurring in the root of American Mayapple (*Podophyllum peltatum*).

Antineoplastics include the immunosuppressant dactinomycin, doxorubicin, epirubicin, bleomycin, mechlorethamine, cyclophosphamide, chlorambucil, ifosfamide. The antineoplastic compounds generally work by chemically modifying a cell's DNA.

Alkylating agents can alkylate many nucleophilic functional groups under conditions present in cells. Cisplatin and carboplatin, and oxaliplatin are alkylating agents. They impair cell function by forming covalent bonds with the amino, carboxyl, sulfhydryl, and phosphate groups in biologically important molecules.

Vinca alkaloids bind to specific sites on tubulin, inhibiting the assembly of tubulin into microtubules (M phase of the cell cycle). The vinca alkaloids include: vincristine, vinblastine, vinorelbine, and vindesine.

Anti-metabolites resemble purines (azathioprine, mercaptopurine) or pyrimidine and prevent these substances from becoming incorporated in to DNA during the "S" phase of the cell cycle, stopping normal development and division. Anti-metabolites also affect RNA synthesis.

Plant alkaloids and terpenoids are derived from plants and block cell division by preventing microtubule function. Since microtubules are vital for cell division, without them, cell division cannot occur. The main examples are vinca alkaloids and taxanes.

Podophyllotoxin is a plant-derived compound which has been reported to help with digestion as well as used to produce two other cytostatic drugs, etoposide and teniposide. They prevent the cell from entering the GI phase (the start of DNA replication) and the replication of DNA (the S phase).

Taxanes as a group includes paclitaxel and docetaxel. Paclitaxel is a natural product, originally known as Taxol and first derived from the bark of the Pacific Yew tree. Docetaxel is a semi-synthetic analogue of paclitaxel. Taxanes enhance stability of microtubules, preventing the separation of chromosomes during anaphase.

Provided herein are methods of treating an individual suffering from cancer or suspected of having cancer comprising administering to the individual the herbal compositions provided herein. The individual can be administered an herbal composition comprising an extract derived from a plant of the genus *Panax*, an extract derived from a fungus of the genus *Ganoderma*, and an extract derived from a plant from the genus *Saussurea*. Alternatively, the individual can be administered a composition comprising an active ingredient consisting essentially of an extract derived from a plant of the genus *Panax*, an extract derived from a fungus of the genus *Ganoderma*, and an extract derived from a plant of the genus *Saussurea*. The composition can be in a dosage form of a solution, a suspension, a liquid, a powder, a granule, an injection, a tablet, a capsule, or a pill. The composition can be administered in an adjuvant setting or administered in a neoadjuvant setting. The methods provided herein can further comprise administering one or more additional anticancer therapies to the individual. These additional anticancer therapies can include, without limitation, alkylating agents, antimetabolites, anthracyclines, plant alkaloids, topoisomerase inhibitors, podophyllotoxin, antibodies, tyrosine kinase inhibitors, hormone treatments, soluble receptors or other antineoplastics. The compositions can additionally include one or more pharmaceutical excipients. In some embodiments, the composition used to treat cancer can be a concentrated extract derived from 8 g of a plant of the genus *Panax*, 8 g of an extract derived from a fungus of the genus *Ganoderma*, and 8 g of an extract derived from a plant from the genus *Saussurea* which has been extracted in 40% ethanol at a temperature of 60° C. for 2 hours. In another embodiment the composition used to treat cancer (for example, liver cancer) can be a concentrated extract derived from 8 g of a plant of the genus *Panax*, 8 g of an extract derived from a fungus of the genus *Ganoderma*, and 8 g of an extract derived from a plant from the genus *Saussurea* which has been extracted in 95% ethanol at a temperature of 60° C. for 2 hours. In another embodiment the composition used to treat cancer (for example, liver cancer) can be a concentrated combined extract derived from 15 g of a plant of the genus *Panax*, 15 g of an extract derived from a fungus of the genus *Ganoderma*, and 15 g of an extract derived from a plant from the genus *Saussurea* whereby the extracts have been extracted individually in 95% ethanol while being refluxed for 2 hours.

Inflammatory or Immune System Disorder

Hypersensitivity disorders are commonly associated with undesirable inflammatory reactions produced by the normal immune system. These reactions may be damaging, uncomfortable, or occasionally fatal. Immunoglobulin E (IgE) and Immunoglobulin G (IgG) are a class of antibody that plays an important role in hypersensitivity disorders. Additionally, IgE has been implicated in immune system responses to most parasitic worms such as *Schistosoma mansoni*, *Trichinella spiralis*, and *Fasciola hepatica*, and may be important during immune defense against certain protozoan parasites such as *Plasmodium falciparum*.

One aspect of the invention provides for methods of using the compositions described herein to treat individuals who have been diagnosed with inflammatory or immune system disorders characterized by IgE-mediated inflammation or who are suspected of having inflammatory or immune system disorders characterized by IgE-mediated inflammation. Common inflammatory or immune system disorders characterized by IgE-mediated inflammation include, but are not limited to, hyper-IgE syndrome, atopic syndrome, eczema, allergic rhinitis, allergy-induced asthma, asthma, food allergies, pollen allergies, animal dander allergies, dust mite allergies, anaphylaxis, allergic conjunctivitis, angioedema, urticaria, eosinophilia, penicillin allergy, cephalosporin allergy, sulfa drug allergy, and drug allergies.

Provided herein are methods of treating an individual suffering from an inflammatory or immune system disorder comprising administering to the individual the herbal compositions provided herein. The individual can be administered an herbal composition comprising an extract derived from a plant of the genus *Panax*, an extract derived from a fungus of the genus *Ganoderma*, and an extract derived from a plant from the genus *Saussurea*. Alternatively, the individual can be administered a composition comprising an active ingredient consisting essentially of an extract derived from a plant of the genus *Panax*, an extract derived from a fungus of the genus *Ganoderma*, and an extract derived from a plant of the genus *Saussurea*. The composition can be in a dosage form of a solution, a suspension, a liquid, a powder, a granule, an injection, a tablet, a capsule, or a pill. The composition can be administered in an adjuvant setting or administered in a neoadjuvant setting. The methods provided herein can further comprise administering one or more additional inflammatory or immune system disorder therapies to the individual. The compositions can additionally include one or more pharmaceutical excipients. In some embodiments, the composition used to treat cancer can be a concentrated extract derived from 8 g of a plant of the genus *Panax*, 8 g of an extract derived from a fungus of the genus *Ganoderma*, and 8 g of an extract derived from a plant from the genus *Saussurea* which has been extracted in 40% ethanol at a temperature of 60° C. for 2 hours. In some embodiments, the composition used to treat cancer can be a concentrated extract derived from 8 g of a plant of the genus *Panax*, 8 g of an extract derived from a fungus of the genus *Ganoderma*, and 8 g of an extract derived from a plant from the genus *Saussurea* which has been extracted in 95% ethanol while being refluxed for 2 hours.

Cachexia

Cachexia, or wasting syndrome, is loss of weight, muscle atrophy, fatigue, weakness, and significant loss of appetite in someone who is not actively trying to lose weight. The formal definition of cachexia is the loss of body mass that cannot be reversed nutritionally even if the affected patient eats more calories, lean body mass will be lost, indicating an underlying pathology. Cachexia is a positive risk factor for death—meaning that if the patient has cachexia, the chance of death from the underlying condition is increased dramatically.

Conditions underlying cachexia include, but are not limited to, cancer, AIDS, chronic obstructive lung disease, congestive heart failure, tuberculosis, familial amyloid polyneuropathy, mercury poisoning (acrodynia) and hormonal deficiency.

Provided herein are methods of treating an individual suffering from cachexia comprising administering to the individual the herbal compositions provided herein. The individual can be administered an herbal composition comprising an extract derived from a plant of the genus *Panax*, an extract derived from a fungus of the genus *Ganoderma*, and an extract derived from a plant from the genus *Saussurea*. Alternatively, the individual can be administered a composition comprising an active ingredient consisting essentially of an extract derived from a plant of the genus *Panax*, an extract derived from a fungus of the genus *Ganoderma*, and an extract derived from a plant of the genus *Saussurea*. The composition can be in a dosage form of a solution, a suspension, a liquid, a powder, a granule, an injection, a tablet, a capsule, or a pill. The composition can be administered in an adjuvant setting or administered in a neoadjuvant setting. The compositions can additionally include one or more pharmaceutical excipients. The methods provided herein can further comprise administering one or more additional cachexia therapies to the individual. The compositions can additionally include one or more pharmaceutical excipients.

EXAMPLES

In order to explore the full potential of the compositions disclosed herein, the compositions were tested in appropriate in vitro and in vivo models of chronic disease. Fifty (50) extracts prepared from forty-three (43) different extraction methods were used for pharmacological activity screening.

Aqueous alcohol with different alcohol concentrations ranging from 0% to 95% was used as an extractant. Key process parameters for each method studied were identified. Extracts prepared with different extraction methods were tested against four in vitro pharmacological action model platforms for purposes of screening (i) the effect of inhibition on HBV antigen expression in HepG2.2.15 (a human hepatocellular carcinoma cell line), (ii) the effect of inhibition on tumor necrosis factor-α (TNF-α) secretion in U937 (a human leukemia cell line), (iii) the effect of inhibition on cell proliferation in four different human liver cancer cell line cells, and (iv) the effect of inhibition on cell proliferation in six human cancer cell line cells (lung, stomach, prostate, colorectal, cervical, and breast), respectively.

Example 1

Extraction and Concentration of Ingredient Raw Materials

This Example details the extraction and concentration of ingredient raw materials from plants and fungi used as part of traditional Chinese medicine. The raw materials used in the formula, (hereinafter named "HXLS formula" or "HXLS" or "formula"), are composed of Baishen (*Panax*; hereinafter named "HXLS-P"; "HXLS-P'" is designated a variant species of *Panax*); Lingzhi (*Ganoderma*; hereinafter named "HXLS-G"); and Snow-Lotus-Flower (*Saussurea*; hereinafter named "HXLS-S"). The component raw materials are decocted with water or aqueous alcohol before use in order to extract the active components from each plant or fungus species. Fifty (50) different extracts were prepared from the formula utilizing different extraction methods such as temperature, varied alcohol concentration of the aqueous alcohol solution, use or nonuse of reflux, and extraction time.

Materials and Methods

95% pure ethanol purchased from Sigma-Aldrich (St. Louis, Mo.). De-ionized (D.I.) water was made in house.

The gas chromatography apparatus used was the Agilent Technologies (Santa Clara, Calif.) model 6890. The High performance liquid chromatography (HPLC) apparatus used was the Harlow Scientific (Arlington, Mass.) model 2695. The machine used to concentrate the extract was the Jasco Inc. (Easton, Md.) rotary evaporator. All glass wares were Pyrex or equivalents.

Numbers in parenthesis following the description of each method indicates test article serial number for each extraction experiment.

Method A

Extraction of HXLS by D.I. water at ambient temperature. Dried and milled *Saussurea* (*Saussurea involucra*), 8 g, *Ganoderma* (*Ganoderna lucidum*) 8 g, and *Panax* (*Panax quinquefolium*) 8 g were mixed together and extracted with 300 mL of D.I. water in a 500 mL round bottom flask. The liquid and solid mixture was kept standing at ambient temperature for 24 hr. With filtration, the solid material (solid material A) was removed and the filtrate was concentrated by rotary evaporation. (796-37-01).

Method B

Extraction of HXLS by D.I. water with reflux from solid material. The solid material A (from method A) was added with 300 mL of D.I. water and the mixture was then heated to reflux for 2 hr. With filtration the solid material was removed and the filtrate was concentrated by rotary evaporation. (796-37-02).

Method C

Extraction of HXLS by D.I. water with reflux from dried and milled ingredients. Dried and milled *Saussurea* (*Saussurea involucra*), 8 g, *Ganoderma Ganoderna lucidum*) 8 g, and *Panax* (*Panax quinquefolium*) 8 g were mixed together and extracted with 300 mL of DI water in a 500 mL round bottom flask. The liquid and solid mixture was then heated to boiling and refluxed for 2 hr. With filtration the solid material was removed and the filtrate was concentrated by rotary evaporation. (796-37-03). Method C was also repeated with another species of *Panax, Panax ginseng* (*Panax'*) and designated as (796-37-03').

Method D

Extraction of HXLS by 40% ethanol at ambient temperature. Dried and milled *Saussurea* (*Saussurea involucra*), 8 g, *Ganoderma* (*Ganoderna lucidum*) 8 g, and *Panax* (*Panax quinquefolium*) 8 g were mixed together and extracted with 300 mL of 40% EtOH in a 500 mL round bottom flask. The mixture was kept standing at ambient temperature for 7 days. With filtration the solid material (solid material D) was removed and the filtrate was concentrated by rotary evaporation. (796-37-04).

Method E

Extraction of HXLS by 40% ethanol with reflux. The solid material D (from method D) was added with 300 mL of 40% EtOH and the liquid and solid mixture was then heated to reflux for 2 hr. With filtration the solid material was removed and the filtrate was concentrated by rotary evaporation. (796-37-05).

Method F

Extraction of HXLS by 40% ethanol at 60° C. Dried and milled *Saussurea* (*Saussurea involucra*), 8 g, *Ganoderma* (*Ganoderna lucidum*) 8 g, and *Panax* (*Panax quinquefolium*) 8 g were mixed together and extracted with 300 mL of 40% ethanol in a 500 mL round bottom flask. The liquid and solid mixture was then heated to 60+2° C. for 2 hr. With filtration, the solid material was removed and the filtrate was concentrated by rotary evaporation. (796-37-06).

Method G

The Extraction of HXLS by 40% Ethanol with reflux. Dried and milled *Saussurea* (*Saussurea involucra*), 8 g, *Ganoderma* (*Ganoderna lucidum*) 8 g, and *Panax* (*Panax quinquefolium*) 8 g were mixed together and extracted with 300 mL of 40% ethanol in a 500 mL round bottom flask. The liquid and solid mixture was then heated to reflux for 2 hr. With filtration the solid material was removed and the filtrate was concentrated by rotary evaporation. (796-37-07).

Method H

Extraction of HXLS by 95% ethanol at ambient temperature. Dried and milled *Saussurea* (*Saussurea involucra*), 8 g, *Ganoderma* (*Ganoderna lucidum*) 8 g, and *Panax* (*Panax quinquefolium*) 8 g were mixed together and extracted with 300 mL of 95% EtOH in a 500 mL round bottom flask. The liquid and solid mixture was kept standing at ambient temperature for 7 days. With filtration the solid material (solid material H) was removed and the filtrate was concentrated by rotary evaporation. (796-37-08).

Method I

Extraction of HXLS by 95% ethanol at reflux. The solid material H (from method H) was added with 300 mL of 40% EtOH and the mixture was then heated to reflux for 2 hr. With filtration the solid material was removed and the filtrate was concentrated by rotary evaporation. (796-37-09).

Method J

Extraction of HXLS by 95% Ethanol at 60° C. Dried and milled *Saussurea* (*Saussurea involucra*), 8 g, *Ganoderma* (*Ganoderna lucidum*) 8 g, and *Panax* (*Panax quinquefo*-

*lium*) 8 g were mixed together and extracted with 300 mL of 95% Ethanol in a 500 mL round bottom flask. The mixture was then heated to 60±2° C. for 2 hr. With filtration the solid material was removed and the filtrate was concentrated by rotary evaporation. (796-37-10).

Method K

The Extraction of HXLS by 95% Ethanol with reflux. Dried and milled *Saussurea* (*Saussurea involucra*), 8 g, *Ganoderma* (*Ganoderna lucidum*) 8 g, and *Panax* (*Panax quinquefolium*) 8 g were mixed together and extracted with 300 mL of 95% Ethanol in a 500 mL round bottom flask. The liquid and solid mixture was then heated to reflux for 2 hr. With filtration the solid material was removed and the filtrate was concentrated by rotary evaporation. (796-37-11). Method K was also repeated with another species of *Panax, Panax ginseng* (*Panax'*) and designated as (796-37-11').

Method L

HXLS-G or HXLS-S or HXLS-P was extracted by D.I. water at ambient temperature.

(1) Dried and milled *Ganoderma* (*Ganoderna lucidum*) 15 g was extracted with 200 mL of D.I. water in a 500 mL round bottom flask. The liquid and solid mixture was kept standing at ambient temperature for 24 hr. With filtration the solid material (solid material L-1) was removed and the filtrate was concentrated by rotary evaporation. (796-37-12).

(2) Dried and milled *Saussurea* (*Saussurea involucra*) 15 g was extracted with 300 mL of D.I. water in a 500 mL round bottom flask. The liquid and solid mixture was kept standing at ambient temperature for 24 hr. With filtration the solid material (solid material L-2) was removed and the filtrate was concentrated by rotary evaporation. (796-37-13).

(3) Dried and milled *Panax* (*Panax quinquefolium*) 15 g was extracted with 150 mL of D.I. water in a 500 mL round bottom flask. The liquid and solid mixture was kept standing at ambient temperature for 24 hr. With filtration the solid material (solid material L-3) was removed and the filtrate was concentrated by rotary evaporation. (796-37-14).

The above-mentioned concentrated filtrates obtained from the extractions of HXLS-G, HXLS-S, and HXLS-P and were mixed together to form a new combined HXLS extraction. (796-37-15).

Method M

HXLS-G or HXLS-S or HXLS-P was extracted by D.I. water with reflux.

(1) The solid material L-1 (from method L (1)) was added with 300 mL of D.I. water and the liquid and solid mixture was then heated to reflux for 2 hr. With filtration the solid material was removed and the filtrate was concentrated by rotary evaporation. (796-37-16).

(2) The solid material L-2 (from method L (2)) was added with 300 mL of D.I. water and the liquid and solid mixture was then heated to reflux for 2 hr. With filtration the solid material was removed and the filtrate was concentrated by rotary evaporation. (796-37-17).

(3) The solid material L-3 (from method L (3)) was added with 300 mL of D.I. water and the liquid and solid mixture was then heated to reflux for 2 hr. With filtration the solid material was removed and the filtrate was concentrated by rotary evaporation. (796-37-18).

The three above-mentioned concentrated filtrates obtained from the extractions of solid material L-1 (HXLs-G), solid material L-2 (HXLs-S), and solid material L-3 (HXLs-P) were mixed together to form a new HXLs extraction. (796-37-19). Method M was also repeated with another species of *Panax, Panax ginseng* (*Panax'*) and designated as (796-37-19').

Method N

HXLS-G or HXLS-S or HXLS-P was extracted by D.I. water with reflux (1) Dried and milled *Ganoderma* (*Ganoderna lucidum*) 15 g was extracted with 200 mL of D.I. water in a 500 mL round bottom flask. The liquid and solid mixture was then heated to reflux for 2 hr. With filtration the solid material was removed and the filtrate was concentrated by rotary evaporation. (796-37-20).

(2) Dried and milled *Saussurea* (*Saussurea involucra*) 15 g was extracted with 300 mL of D.I. water in a 500 mL round bottom flask. The liquid and solid mixture was then heated to reflux for 2 hr. With filtration the solid material was removed and the filtrate was concentrated by rotary evaporation. (796-37-21).

(3) Dried and milled *Panax* (*Panax quinquefolium*) 15 g was extracted with 150 mL of D.I. water in a 500 mL round bottom flask. The liquid and solid mixture was then heated to reflux for 2 hr. With filtration the solid material was removed and the filtrate was concentrated by rotary evaporation. (796-37-22).

The three above-mentioned concentrated filtrates obtained from the extractions of HXLS-G, HXLS-S, and HXLS-P were mixed together to form a new HXLS extraction. (796-37-23). Method N was also repeated with another species of *Panax, Panax ginseng* (*Panax'*) and designated as (796-37-23').

Method O

HXLS-G or HXLS-S or HXLS-P was extracted by 40% ethanol at 60° C.

(1) Dried and milled *Ganoderma* (*Ganoderna lucidum*) 15 g was extracted with 200 mL of 40% ethanol in a 500 mL round bottom flask. The liquid and solid mixture was then heated to 60±2° C. for 2 hr. With filtration the solid material was removed and the filtrate was concentrated by rotary evaporation. (796-37-24).

(2) Dried and milled *Saussurea* (*Saussurea involucra*) 15 g was extracted with 300 mL of 40% ethanol in a 500 mL round bottom flask. The liquid and solid mixture was then heated to 60±2° C. for 2 hr. With filtration the solid material was removed and the filtrate was concentrated by rotary evaporation. (796-37-25).

(3) Dried and milled *Panax* (*Panax quinquefolium*) 15 g was extracted with 150 mL of 40% Ethanol in a 500 mL round bottom flask. The liquid and solid mixture was then heated to 60±2° C. for 2 hr. With filtration the solid material was removed and the filtrate was concentrated by rotary evaporation. (796-37-26).

The three above-mentioned concentrated filtrates obtained from the extractions of HXLS-G, HXLS-S, and HXLS-P were mixed together to form a new HXLS extraction. (796-37-27). Method O was also repeated with another species of *Panax, Panax ginseng* (*Panax'*), and designated as (796-37-27').

Method P

HXLS-G or HXLS-S or HXLS-P was extracted by 40% ethanol with reflux (1) Dried and milled *Ganoderma* (*Ganoderna lucidum*) 15 g was extracted with 200 mL of 40% ethanol in a 500 mL round bottom flask. The liquid and solid mixture was then heated to reflux for 2 hr. With filtration the solid material was removed and the filtrate was concentrated by rotary evaporation. (796-37-28).

(2) Dried and milled *Saussurea* (*Saussurea involucra*) 15 g was extracted with 300 mL of 40% ethanol in a 500 mL round bottom flask. The liquid and solid mixture was then heated to reflux for 2 hr. With filtration the solid material was removed and the filtrate was concentrated by rotary evaporation. (796-37-29).

(3) Dried and milled *Panax* (*Panax quinquefolium*) 15 g was extracted with 150 mL of 40% ethanol in a 500 mL round bottom flask. The liquid and solid mixture was then heated to reflux for 2 hr. With filtration the solid material was removed and the filtrate was concentrated by rotary evaporation. (796-37-30).

The three above-mentioned concentrated filtrates obtained from the extractions of HXLS-G, HXLS-S, and HXLS-P were mixed together to form a new HXLS extraction. (796-37-31). Method P was also repeated with another species of *Panax, Panax ginseng* (*Panax'*), and designated as (796-37-31').

Method Q

HXLS-G or HXLS-S or HXLS-P was extracted by 95% ethanol with reflux (1) Dried and milled *Ganoderma* (*Ganoderna lucidum*) 15 g was extracted with 200 mL of 95% ethanol in a 500 mL round bottom flask. The liquid and solid mixture was then heated to reflux for 2 hr. With filtration the solid material was removed and the filtrate was concentrated by rotary evaporation. (796-37-32).

(2) Dried and milled *Saussurea* (*Saussurea involucra*) 15 g was extracted with 300 mL of 95% ethanol in a 500 mL round bottom flask. The liquid and solid mixture was then heated to reflux for 2 hr. With filtration the solid material was removed and the filtrate was concentrated by rotary evaporation. (796-37-33).

Dried and milled *Panax* (*Panax quinquefolium*) 15 g was extracted with 150 mL of 95% ethanol in a 500 mL round bottom flask. The liquid and solid mixture was then heated to reflux for 2 hr. With filtration the solid material was removed and the filtrate was concentrated by rotary evaporation. (796-37-34).

The three above-mentioned concentrated filtrates obtained from the extractions of HXLS-G, HXLS-S, and HXLS-P were mixed together to form a new HXLS extraction. (796-37-35). Method Q was also repeated with another species of *Panax, Panax ginseng* (*Panax'*), and designated as (796-37-35').

Method R

HXLS-G or HXLS-S or HXLS-P was extracted by 40% ethanol (1) Dried and milled *Ganoderma* (*Ganoderna lucidum*) 15 g was extracted with 200 mL of 40% ethanol in a 500 mL round bottom flask. The liquid and solid mixture was kept standing at ambient temperature for 7 days. With filtration the solid material was removed and the filtrate was concentrated by rotary evaporation. (796-37-36).

(2) Dried and milled *Saussurea* (*Saussurea involucra*) 15 g was extracted with 300 mL of 40% Ethanol in a 500 mL round bottom flask. The liquid and solid mixture was kept standing at ambient temperature for 7 days. With filtration the solid material was removed and the filtrate was concentrated by rotary evaporation. (796-37-37).

(3) Dried and milled *Panax* (*Panax quinquefolium*) 15 g was extracted with 150 mL of 40% ethanol in a 500 mL round bottom flask. The liquid and solid mixture was kept standing at ambient temperature for 7 days. With filtration the solid material was removed and the filtrate was concentrated by rotary evaporation. (796-37-38).

The three above-mentioned concentrated filtrates obtained from the extractions of HXLS-G, HXLS-S, and HXLS-P were mixed together to form a new HXLS extraction. (796-37-39). Method R was also repeated with another species of *Panax, Panax ginseng* (*Panax'*), and designated as (796-37-39').

Method S

HXLS-G or HXLS-S or HXLS-P was extracted by 40% ethanol (1) Dried and milled *Ganoderma* (*Ganoderna lucidum*) 15 g was extracted with 200 mL of 40% ethanol in a 500 mL round bottom flask. The liquid and solid mixture was kept standing at ambient temperature for 7 days and then heated to reflux for 2 hr. With filtration the solid material was removed and the filtrate was concentrated by rotary evaporation. (796-37-40).

(2) Dried and milled *Saussurea* (*Saussurea involucra*) 15 g was extracted with 300 mL of 40% ethanol in a 500 mL round bottom flask. The liquid and solid mixture was kept standing at ambient temperature for 7 days then heated to reflux for 2 hr. With filtration the solid material was removed and the filtrate was concentrated by rotary evaporation. (796-37-41).

(3) Dried and milled *Panax* (*Panax quinquefolium*) 15 g was extracted with 150 mL of 40% ethanol in a 500 mL round bottom flask. The liquid and solid mixture was kept standing at ambient temperature for 7 days then heated to reflux for 2 hr. With filtration the solid material was removed and the filtrate was concentrated by rotary evaporation. (796-37-42).

The three above-mentioned concentrated filtrates obtained from the extractions of HXLS-G, HXLS-S, and HXLS-P were mixed together to form a new HXLS extraction. (796-37-43). Method S was also repeated with another species of *Panax, Panax ginseng* (*Panax'*), and designated as (796-37-43').

Example 2

In Vitro Pharmacological Study of the HXLS Formula Extracts

The detailed pharmacological activities of the 50 extracts prepared from the HXLS formula in Example 1, (hereinafter referred to as the "HXLS extracts"), were tested against four cell based pharmacological action model platforms, including HBV antigen expression, inflammation cytokine secretion, proliferation of liver cancer cells (four different human liver cancer cell lines), and proliferation of other cancer cells (six different human cancer cell lines of lung, stomach, prostate, colorectal, cervical, and breast cancers, respectively). Current in vitro cellular assay results showed that, among the 50 extracts, samples numbered 796-37-19 and 796-37-23 exhibited better anti-HBV activity; samples numbered 796-37-06 and 796-37-11 exhibited better anti-TNF-α activity; samples numbered 796-37-35, 796-37-10, and 796-37-06 exhibited better inhibitory activity on human liver cancer cell proliferation; and samples numbered 796-37-16, and 796-37-06 exhibited better inhibitory activity on cell proliferation of the above-mentioned six cancers. Based on the in vitro results, selected samples were submitted for additional in vivo mice studies for liver and immune diseases. Sample numbered 796-37-03, 796-37-06, and 796-37-11 exhibited positive results for anti-liver inflammation, anti-liver cancer, and chemo-protection; furthermore 796-27-03 exhibited positive results for specialized immune response.

Materials and Methods

Test Articles Preparation and Nomenclature

The ingredient raw materials of the HXLS formula were extracted and prepared as detailed above in Example 1. The 50 HXLS extracts along with their ingredient raw materials and extraction conditions are listed in Table 1. According to the genus name of the ingredient raw material, the extracts are referenced by code names HXLS-P, HXLS-G, and HXLS-S for the extracts of Baishen, Lingzhi, and Snow-Lotus-Flower, respectively; HXLS-GSP for the extracts of the mixture of the three ingredient raw materials, which are mixed together before extraction; HXLS-G+S for the mixture of HXLS-G and HXLS-S; HXLS-G+P for the mixture of HXLS-G and HXLS-P; HXLS-P+S for the mixture of HXLS-P and HXLS-S; and HXLS-G+S+P for the mixture of HXLS-G, HXLS-S, and HXLS-P.

TABLE 1

List of the 50 extracts derived from the HXLS formula for pharmacology study along with their raw material and extraction information. Test articles used in anti-HBV activity screening study are marked with boldfaced test article serial numbers.

| No. | Raw Material | Test article | Extraction solvent | Extraction Temperature |
|---|---|---|---|---|
| 1 | HXLS-GSP | 796-37-01 | $H_2O$ | RT |
| 2 | HXLS-GSP | 796-37-02 | | RT-reflux |
| 3 | HXLS-GSP | 796-37-03 | | reflux |
| 4 | HXLS-GSP' | 796-37-03' | | reflux |
| 5 | HXLS-GSP | 796-37-04 | 40% EtOH | RT |
| 6 | HXLS-GSP | 796-37-05 | | RT-refluex |
| 7 | HXLS-GSP | 796-37-06 | | 60° C. |
| 8 | HXLS-GSP | 796-37-07 | | reflux |
| 9 | HXLS-GSP | 796-37-08 | 95% EtOH | RT |
| 10 | HXLS-GSP | 796-37-09 | | RT-refluex |
| 11 | HXLS-GSP | 796-37-10 | | 60° C. |
| 12 | HXLS-GSP | 796-37-11 | | reflux |
| 13 | HXLS-GSP' | 796-37-11' | | reflux |
| 14 | HXLS-G | 796-37-12 | $H_2O$ | RT |
| 15 | HXLS-S | 796-37-13 | | RT |
| 16 | HXLS-P | 796-37-14 | | RT |
| 17 | HXLS-G + S + P | 796-37-15 | | RT |
| 18 | HXLS-G | 796-37-16 | $H_2O$ | RT-reflux |
| 19 | HXLS-S | 796-37-17 | | RT-reflux |
| 20 | HXLS-P | 796-37-18 | | RT-reflux |
| 21 | HXLS-G + S + P | 796-37-19 | | RT-reflux |
| 22 | HXLS-G + S + P' | 796-37-19' | | RT-reflux |
| 23 | HXLS-G | 796-37-20 | $H_2O$ | reflux |
| 24 | HXLS-S | 796-37-21 | | reflux |
| 25 | HXLS-P | 796-37-22 | | reflux |
| 26 | HXLS-G + S + P | 796-37-23 | | reflux |
| 27 | HXLS-G + S + P' | 796-37-23' | | reflux |
| 28 | HXLS-G | 796-37-24 | 40% EtOH | 60° C. |
| 29 | HXLS-S | 796-37-25 | | 60° C. |
| 30 | HXLS-P | 796-37-26 | | 60° C. |
| 31 | HXLS-G + S + P | 796-37-27 | | 60° C. |
| 32 | HXLS-G + S + P' | 796-37-27' | | 60° C. |
| 33 | HXLS-G | 796-37-28 | 40% EtOH | reflux |
| 34 | HXLS-S | 796-37-29 | | reflux |
| 35 | HXLS-P | 796-37-30 | | reflux |
| 36 | HXLS-G + S + P | 796-37-31 | | reflux |
| 37 | HXLS-G + S + P' | 796-37-31' | | reflux |
| 38 | HXLS-G | 796-37-32 | 95% EtOH | reflux |
| 39 | HXLS-S | 796-37-33 | | reflux |
| 40 | HXLS-P | 796-37-34 | | reflux |
| 41 | HXLS-G + S + P | 796-37-35 | | reflux |
| 42 | HXLS-G + S + P' | 796-37-35' | | reflux |
| 43 | HXLS-G | 796-37-36 | 40% EtOH | RT Soak |
| 44 | HXLS-S | 796-37-37 | | RT Soak |
| 45 | HXLS-P | 796-37-38 | | RT Soak |
| 46 | HXLS-G + S + P | 796-37-39 | | RT Soak |
| 47 | HXLS-G | 796-37-40 | 40% EtOH | RT Soak-reflux |
| 48 | HXLS-S | 796-37-41 | | RT Soak-reflux |
| 49 | HXLS-P | 796-37-42 | | RT Soak-reflux |
| 50 | HXLS-G + S + P | 796-37-43 | | RT Soak-reflux |

Cell Lines and Cell Culture

HBV Producing Cells

Hepatitis B virus producing cell lines, Hep G2.2.15 and 1.3ES8, which express the ayw and adw genotypes of Hepatitis B, respectively, were used in this study. These cells were grown in Dulbecco's Modified Eagle Medium (DMEM, Gibco), supplemented with 10% fetal bovine serum. Cells were cultured at 37° C. in a moist atmosphere containing 5% CO2.

TNF-α Producing Cells

The human myeloid leukemia cell line, U937, obtained from the American Type Culture Collection (Rockville, Md.) was used in this study. The cells were cultured in the RPMI-1640 medium containing 10% FCS at 37° C., 5% CO2 and maintained in an exponential growth status.

Human Hepatocellular Carcinoma Cells

Four human hepatoma cell lines, HepG2, Hep3B, HuH7, and PLC/PRF/5, obtained from Bioresource Collection and Research Center, Hsinchu, Taiwan (BCRC) were used in this study. These cells were grown in Minimum Essential Medium Eagle with 2 mM L-glutamine and Earle's BSS (adjusted to contain 1.5 g/L sodium bicarbonate, 0.1 mM non-essential amino acids, and 1.0 mM sodium pyruvate), supplemented with 10% fetal bovine serum (Gibco/BRL, Invitrogen). Cells were cultured at 37° C. in a humidified incubator with 5% CO2.

Other Human Cancer Cells

Six human cancer cell lines, A549, AGS, PC-3, HT29, HeLa, and MCF-7, which are lung, stomach, prostate, colorectal, cervical, and breast cancer cell lines, respectively, obtained form BCRC were used in this study. These cells were grown in conventional media (Gibco/BRL, Invitrogen) listed in Table 2 and cultured at 37° C. in a humidified atmosphere with 5% CO2 in air.

TABLE 2

Culture media for six human cancer cell lines.

| Cancer type | Cell line | Culture Medium |
|---|---|---|
| Lung | A549 | 90% Ham's F-12K medium (21127) + 10% FBS |
| Stomach | AGS | 90% Ham's F-12K medium (21127) + 10% FBS |
| Prostate | PC-3 | 90% Ham's F-12K medium (21127) + 10% FBS |
| Colorectal | HT29 | 90% RPMI-1640 + 10% FBS |
| Cervical | HeLa | 90% MEM (Eagle) with Earle's BSS, 2 mM L-glutamine, 0.1 mM NEAA, and 1.0 mM sodium pyruvate + 10% FBS |
| Breast | MCF-7 | 90% MEM (Eagle) with Earle's BSS, 2 mM L-glutamine, 0.1 mM NEAA, and 1.0 mM sodium pyruvate + 10% FBS |

Anti-HBV Activities of HXLS Extracts on HBV Producing Cells

Hep G2.2.15

The Hep G2.2.15 cells were seeded at 3×104 cells/well into 96-well culture plates and incubated at 37° C. in 5% CO2 overnight. After 3 to 4 days, the confluent cultures were cultured at 37° C. for another 3 to 5 days for HBV surface antigen (HBsAg) and HBV e-antigen (HBeAg) induction. Various concentrations of test articles including the positive control substance were then added during the 72 hrs induction period. The cultured media were harvested by centrifugation and the levels of HBsAg and HBeAg were analyzed with commercial enzyme-linked immunosorbant assay (ELISA) kits for HBsAg qualitative testing (General Biologicals Corp., SURASE B-96 (TMB)) and that for HBeAg qualitative testing (General Biologicals Corp., EASE BN-96

(TMB)), respectively. The activity expressed in terms of the efficiency of antigen secretion in percentage (hereinafter referred to as "relative activity") was calculated with the equation > Relative activity (%)=The ratio of the amount of antigen in the cultured medium with treatment to that without treatment×100.

Cell viability was assayed by the MTT method. Adefovir dipivoxil (ADFV, Patheon Inc., Canada), an antiviral agent, was used as positive control.

2.2.1.2 Hep G2.2.15 and 1.3ES8

The Hep G2.2.15 and 1.3ES8 cells were seeded at 1×105 cells/well into 96-well culture plates and incubated at 37° C. in 5% CO2 overnight. Various concentrations of test articles including the positive control substance were then added into culture plates and the cells were cultured for 2 days. After 2 days of incubation, a half of the volume of test articles added was added into culture plates and the cells were cultured for another 2 days. The cultured media were harvested by centrifugation and the levels of HBsAg and HBeAg were analyzed with commercial enzyme-linked immunosorbant assay (ELISA) kits for HBsAg qualitative testing (General Biologicals Corp., SURASE B-96 (TMB)) and that for HBeAg qualitative testing (General Biologicals Corp., EASE BN-96 (TMB)), respectively. The activity expressed in terms of the degree of reduction of antigen secretion in percentage (hereinafter referred to as "Inhibition rate") was calculated with the equation > Inhibition rate (%)=(1−the ratio of the amount of antigen in the cultured medium with treatment to that without treatment)×100

Cell viability was assayed by the MTT method. An antiviral agent, CPB (50 μg/ml) was used as positive control.

Hep G2.2.15 and 1.3ES8

The Hep G2.2.15 and 1.3ES8 cells were seeded at 1×105 cells/well into 96-well culture plates and incubated at 37° C. in 5% CO2 overnight. Various concentrations of test articles including the positive control substance were then added into culture plates and the cells were cultured for 2 days. After 2 days of incubation, a half of the volume of test articles added was added into culture plates and the cells were cultured for another 2 days. The cultured media were harvested by centrifugation and the levels of HBsAg and HBeAg were analyzed with commercial enzyme-linked immunosorbant assay (ELISA) kits for HBsAg qualitative testing (General Biologicals Corp., SURASE B-96 (TMB)) and that for HBeAg qualitative testing (General Biologicals Corp., EASE BN-96 (TMB)), respectively. The activity expressed in terms of the degree of reduction of antigen secretion in percentage (hereinafter referred to as "Inhibition rate") was calculated with the equation > Inhibition rate (%)=(1−the ratio of the amount of antigen in the cultured medium with treatment to that without treatment)×100

Cell viability was assayed by the MTT method. An antiviral agent, CPB (50 μg/ml) was used as positive control.

Anti-Inflammation Activity of HXLS Extracts on U937 Cells

Differentiated U937 cells were seeded at 1.6×105 cells/well into 96-well culture plates. Various concentrations of test articles were then added and the cells were incubated at 37° C. in 5% CO2 for 30 minutes. Lipopolysaccharide (100 ng/ml) was then added into the culture plates and the cells were incubated for another 4 hours. The cultured media were harvested for TNF-α analysis with commercial assay kits (R&D Systems (Minneapolis, Minn.)). Results were calculated with GraFit Data Analysis Software and expressed as IC50 (μg/ml). The cell viability assay was performed by the MTT method: cells were incubated with 45 μl of 5 mg/ml MTT for 1 hour at 37° C., then 150 μl of DMSO was added to dissolve the crystals, and then OD570 was measured with ELISA reader (Thermo Labsystems, Multiskan Ascent). Cell viability was expressed in percentage of viable LPS-stimulated cells.

Anti Proliferation Activity of HXLS Extracts on Human Cancer Cells

Human cancer cell line cells were seeded at 1×104 cells/well in 96-well culture plates and incubated overnight at 37° C. in 5% CO2. Various concentrations of test articles and the control substance were then added and the cells were cultured for additional 24, 48 or 72 hrs. The culture medium was removed, and the cultured cells were washed with warm PBS. The MTT solution was added into each assayed well and the culture plates were incubated at 37° C. for 2 to 4 hrs. The converted dye was dissolved with SDS at 37° C. overnight after removal of the medium. Absorbance of the converted dye was measured at a wavelength of 570 nm with background subtraction at 650 nm (Spectra max 340PC, Molecular Device). The IC50 values were calculated by a typical dose-response curve with a variable slope parameter (Sigmaplot 8.0, Four Parameter Logistic Equation):

(a) Inhibition Concentration (IC) Determination Blank is Exclusive

> Cell viability(%)=(O.D. Value of Sample/O.D. Value of control)*100%

> IC (%)=100%−Viability(%)

(b) Growth Inhibition Concentration (GI) Determination Blank is Exclusive

> Growth rate(%):(Tx−T0)/(Cx−T0)×100

> GI (%)=100%−Growth rate(%)

T0: 0 hr treatment control group

Cx: each 24, 48, 72 hr control group

Tx: each 24, 48, 72 hr treatment group

Results

Anti-HBV Activity of HXLS Extracts on HBV Producing Cells

To test the activity of the HXLS extracts on the HBV components, each extract sample was incubated with the Hep G2.2.15 cells carrying HBV genome. The cell viability was determined by the MTT method and the amount of HBsAg and that of HBeAg were measured with ELISA. In this study, 20 HXLS extract samples were tested. Results showed that no cell toxicity of the test articles at concentration 125 μg/ml or lower were observed. The better anti-HBV activities were obtained in test articles numbered 796-37-19 and 796-37-23, and their relative activities of HBeAg expression at 125 μg/ml were 45.2% and 55.5%, respectively (Table 3.).

TABLE 3

Anti-HBV activity of HXLS extracts on Hep G2.2.15 cells. Results were expressed as relative activity (%) which was the ratio of (+)drug/(−)drug. Three concentrations from serial dilution of each extract sample were assayed. Adefovir dipivoxil was used as a positive control. The left and middle columns indicate the anti-HBeAg and Anti-HBsAg activities, respectively. The right columns indicate the cytotoxicity results.

| Table | (ug/ml) | (+) drug/(−) drug (Ratio)* | | |
|---|---|---|---|---|
| | | HBeAg | HBsAg | MTT |
| 796-37-01 | 5 | 1.079 | 1.015 | 1.001 |
| | 25 | 1.098 | 1.417 | 1.019 |
| | 125 | 1.036 | 1.322 | 1.021 |
| 796-37-13 | 5 | 1.076 | 1.000 | 0.989 |
| | 25 | 0.966 | 0.990 | 1.010 |
| | 125 | 0.736 | 0.895 | 1.013 |
| 796-37-21 | 5 | 0.910 | 0.982 | 1.040 |
| | 25 | 0.834 | 0.984 | 0.997 |
| | 125 | 0.856 | 1.256 | 1.000 |
| 796-37-33 | 5 | 0.947 | 1.004 | 1.024 |
| | 25 | 0.882 | 0.888 | 0.986 |
| | 125 | 0.870 | 0.823 | 0.964 |
| 796-37-34 | 5 | 1.087 | 0.935 | 1.023 |
| | 25 | 0.984 | 0.855 | 0.983 |
| | 125 | 0.861 | 0.741 | 0.976 |
| 796-37-35 | 5 | 0.960 | 0.913 | 1.012 |
| | 25 | 0.907 | 0.814 | 0.984 |
| | 125 | 0.856 | 0.721 | 0.967 |
| 796-37-03 | 5 | 0.947 | 0.809 | 0.975 |
| | 25 | 0.910 | 0.807 | 0.963 |
| | 125 | 0.786 | 0.678 | 0.987 |
| 796-37-19 | 5 | 0.982 | 0.897 | 0.970 |
| | 25 | 0.901 | 0.862 | 0.975 |
| | 125 | *0.452* | 0.754 | 0.991 |
| 796-37-23 | 5 | 0.913 | 0.843 | 0.967 |
| | 25 | 0.817 | 0.781 | 1.021 |
| | 125 | *0.555* | 0.706 | 0.971 |
| Adefovir | 0.2 uM | 0.991 | 0.908 | 0.961 |
| | 1 uM | 0.992 | 0.810 | 0.953 |
| | 5 uM | 0.843 | 0.706 | 0.975 |

These HXLS extracts were also tested on Hep G2.2.15 and 1.3ES8 cells. The test results showed that almost all test articles except test article numbered 796-37-12 have no cell toxicity at 200 μg/ml. Higher anti-HBV activities were observed on 1.3ES8 cells than on Hep G2.2.15 cells (Table 4). Better anti-HBV activities were observed for test articles numbered 796-37-13, 796-37-16, 796-37-17, and 796-37-23.

Anti-Inflammation Effect of HXLS Extracts on Tnf-α Production in U937 Cells

To evaluate the anti-inflammatory activity of HXLS extracts, differentiated U937 cells were incubated with the extract samples and stimulated with LPS. The cell viability was determined with MTT assays, and the secretion of TNF-α was measured with ELISA. Thirty-one HXLS extracts were assayed. Results show that no cell toxicity of the HXLS extracts was observed at 900 μg/ml and six of the HXLS extracts exhibited inhibitory activity (IC50<200 μg/ml) on TNF-α secretion, which are, from high to low potency order, test articles numbered 796-37-06, 796-37-11, 796-37-10, 796-37-25, 796-37-35, and 796-37-29. Table 5 shows that the extracts prepared from three ingredient raw material with 95% ethanol aqueous solution, whether which are prepared from extraction of the mixture of three ingredient raw materials (HXLS-GSP), i.e., test articles numbered 796-37-10 and 796-37-11 or it is prepared by mixing separate extracts prepared from extractions of single ingredient raw materials (HXLS-G+S+P), i.e., test article numbered 796-37-35, all exhibited anti-inflammation activities. While with 40% ethanol aqueous solution, only the extract prepared from extraction of HXLS-GSP with extraction temperature at 60° C., i.e., test article numbered 796-37-06 exhibited anti-inflammation activities.

TABLE 4

Anti-HBV activity of HXLS extracts on Hep G2.2.15 and 1.3ES8 cells. Results were expressed as inhibition rate (%). 200 μg/ml except 796-37-12 (8 μg/ml) of each samples were assayed. CPB (50 μg/ml) was used as a positive control. The rows of test articles exhibiting higher anti-HBeAg and Anti-HBsAg activities are marked bold and italic.

| Test article | Inhibition ratio (%) | | | |
|---|---|---|---|---|
| (200 μg/ml) | HepG2.2.15 | | 1.3ES-8 | |
| AVG | HBs Ag | HBe Ag | HBs Ag | HBe Ag |
| 796-37-01 | 26.42 | 20.7 | 38.87 | 36.65 |
| 796-37-03 | 32.75 | 23.56 | 39.79 | 33.62 |
| 796-37-10 | 31.68 | 24.32 | 42.86 | 31.81 |
| 796-37-11 | NI | 28.08 | 10.83 | 42.97 |
| 796-37-12 (8 μg/ml) | <10 | 34.21 | 44 | <10 |
| 796-37-13 | *34.92* | *31.85* | *54.2* | *46.56* |
| 796-37-14 | 30.37 | 20.27 | 42.13 | 39.31 |
| 796-37-15 | 24.17 | 30.56 | 41.46 | 42.97 |
| 796-37-16 | *33.79* | *26.85* | *53.57* | *31.35* |
| 796-37-17 | *43.61* | *33.4* | *52.91* | *38.75* |
| 796-37-18 | 12.58 | <10 | 37.28 | 19.27 |
| 796-37-19 | 38.36 | 16.19 | 42.8 | 31.73 |
| 796-37-20 | 39.79 | 19.26 | 41.78 | 29.76 |
| 796-37-21 | 36.09 | 33.01 | 34.99 | 37.95 |
| 796-37-22 | 23.3 | 12.26 | NI | 18.16 |
| 796-37-23 | *34.71* | *28.12* | *50* | *43.97* |
| 796-37-32 | NI | 24.77 | NI | 19.96 |
| 796-37-33 | 28.86 | 22.4 | 14.4 | 27.55 |
| 796-37-34 | <10 | 14.09 | 20.06 | 16.94 |
| 796-37-35 | 22.14 | 30.43 | <10 | 48.34 |
| CPB (50 μg/ml) | 81.42 | 58.54 | 65.24 | 42.03 |

NI: has no inhibiting activity
CPB: positive control in this assay

TABLE 5

Anti-inflammation effect of HXLS extracts on TNF-α production in U937 cells.

| Material | Test articles | IC50 (μg/ml) |
|---|---|---|
| HXLSGBP | 796-37-01 | >900 |
| | 796-37-02 | >900 |
| | 796-37-03 | >900 |
| | 796-37-06 | 121 ± 10 |
| | 796-37-07 | 522 ± 117 |
| | 796-37-10 | 156 ± 50 |
| | 796-37-11 | 125 ± 21 |
| HXLSG | 796-37-12 | >900 |
| | 796-37-16 | >500 |
| | 796-37-20 | >900 |
| | 796-37-24 | 312 ± 107 |
| | 796-37-28 | >500 |
| | 796-37-32 | 260 ± 87 |
| HXLSS | 796-37-13 | >900 |
| | 796-37-17 | 558 ± 342 |
| | 796-37-21 | >900 |
| | 796-37-25 | 158 ± 82 |
| | 796-37-29 | 185 ± 37 |
| | 796-37-33 | 204 ± 29 |
| HXLSP | 796-37-14 | >900 |
| | 796-37-18 | >900 |
| | 796-37-22 | >900 |
| | 796-37-26 | 378 ± 75 |
| | 796-37-30 | 467 ± 93 |
| | 796-37-34 | 401 ± 16 |
| HXLSGSP | 796-37-15 | >900 |
| | 796-37-19 | >900 |
| | 796-37-23 | >900 |
| | 796-37-27 | 278 ± 75 |
| | 796-37-31 | 419 ± 131 |
| | 796-37-35 | 161 ± 3 |
| (μg/ml) | <200 | 200-500 | >500 |

Anti Proliferation Activity of HXLS Extracts on Four Human Hepatocellular Carcinoma Cells To evaluate the anti-proliferation activity of HXLS extracts on liver cancer cells, different liver cancer cell lines were incubated with the extract samples for 24, 48, or 72 hrs. The cell viability was determining with MTT assays. The anti-proliferation activity was expressed in terms of IC50 and GI50, which are defined as follows

IC50 the half maximal inhibitory concentration at which the degree of reduction of cell viability reaches 50%. The cell viability at time is expressed in terms of the ratio of the amount of viable cells in the cell culture with treatment at time=t to that of the cell culture without treatment at time=t. The degree of reduction of cell viability is defined as Degree of reduction of cell viability(%)=(1−cell viability)×100

GI50: the half maximal inhibitory concentration at which the degree of reduction of growth rate reaches 50%. The cell growth rate is expressed in terms of the ratio of the amount of viable cells in the cell culture with treatment at time=t to that of the cell culture without treatment at time=0

Degree of reduction of growth rate(%)=(1−cell growth rate)×100

Four most commonly used human hepatocellular carcinoma (HCC) cell lines, Hep3B, HepG2, PLC/PRF/5, and Huh7, were used in this study. Results showed that from high to low potency order, test articles numbered 796-37-35, 796-37-(16+29), 796-37-10, 796-37-06 (as listed in Tables 6a and 6b) exhibited potent anti-HCC activities.

TABLE 6a

Anti-proliferation effect of HXLS-GSP extracts on four human hepatocellular carcinoma cells.

| Material | Test articles | μg/ml | time | Hep3B | HepG2 | PLC/PRF/5 | Huh7 |
|---|---|---|---|---|---|---|---|
| HXLS-GSP | 796-37-01 | $IC_{50}$ | 24 hr | | | | |
| | | | 48 hr | | | | >750 |
| | | | 72 hr | 500-750 | | | 250-500 |
| | | $GI_{50}$ | 24 hr | | | | |
| | | | 48 hr | | | | >750 |
| | | | 72 hr | 100-250 | | | 100-250 |
| | 796-37-02 | $IC_{50}$ | 24 hr | | | | |
| | | | 48 hr | >750 | | | |
| | | | 72 hr | >750 | | | 500-750 |
| | | $GI_{50}$ | 24 hr | | | | |
| | | | 48 hr | <10 | | | |
| | | | 72 hr | 100-250 | | | 500-750 |
| | 796-37-03 | $IC_{50}$ | 24 hr | | <750 | | |
| | | | 48 hr | | | | >750 |
| | | | 72 hr | | | | 261.2 ± 44.6 |
| | | $GI_{50}$ | 24 hr | | 50-100 | | |
| | | | 48 hr | | | | >750 |
| | | | 72 hr | | | | 100-250 |
| | 796-37-06 | $IC_{50}$ | 24 hr | | >750 | | |
| | | | 48 hr | 250-500 | 114.2 ± 2.4 | | >750 |
| | | | 72 hr | 346.7 ± 73.3 | 120.1 ± 2.7 | | 100-250 |
| | | $GI_{50}$ | 24 hr | | 45.2 ± 7.6 | | |
| | | | 48 hr | 211.1 ± 30.5 | 114.2 ± 2.4 | | >750 |
| | | | 72 hr | 50-100 | 50-100 | | 50-100 |
| | 796-37-07 | $IC_{50}$ | 24 hr | | >750 | | |
| | | | 48 hr | | | | >750 |
| | | | 72 hr | | | | 259.2 ± 30.2 |
| | | $GI_{50}$ | 24 hr | | 50-100 | | |
| | | | 48 hr | | | | 500-750 |
| | | | 72 hr | | | | 100-250 |
| | 796-37-10 | $IC_{50}$ | 24 hr | | | | |
| | | | 48 hr | | >750 | | >750 |
| | | | 72 hr | 232.6 ± 52.3 | 250-500 | >750 | ≈250 |
| | | $GI_{50}$ | 24 hr | | | | |
| | | | 48 hr | | 250-500 | | 99.0 ± 72.3 |
| | | | 72 hr | 10-50 | 100-250 | 10-50 | 50-700 |
| | 796-37-11 | $IC_{50}$ | 24 hr | | | | |
| | | | 48 hr | >750 | 500-750 | | >750 |
| | | | 72 hr | 250-500 | 433.7 ± 66.0 | 500-750 | 250-500 |
| | | $GI_{50}$ | 24 hr | | | | |
| | | | 48 hr | 100-250 | 250-500 | | 135.7 ± 24.6 |
| | | | 72 hr | 100-250 | 433.7 ± 66.0 | <10 | 100-250 |
| | | (μg/ml) | | | <100 | 100-500 | >500 |

TABLE 6b

Anti-proliferation effect of HXLS-G + S + P on four human hepatocellular carcinoma cells.

| Material | Test articles | μg/ml | time | Hep3B | HepG2 | PLC/PRF/5 | Huh7 |
|---|---|---|---|---|---|---|---|
| HXLS-G + S + P | 796-37-23 | $IC_{50}$ | 24 hr | | | | |
| | | | 48 hr | | | | >750 |
| | | | 72 hr | | | | 131.8 ± 1.8 |

TABLE 6b-continued

Anti-proliferation effect of HXLS-G + S + P on four human hepatocellular carcinoma cells.

| Material | Test articles | µg/ml | time | Hep3B | HepG2 | PLC/PRF/5 | Huh7 |
|---|---|---|---|---|---|---|---|
| | 796-37-27 | $GI_{50}$ | 24 hr | | | | |
| | | | 48 hr | | | | >750 |
| | | | 72 hr | | | | 50-100 |
| | | $IC_{50}$ | 24 hr | | | | |
| | | | 48 hr | | | | >750 |
| | | | 72 hr | 500-750 | | | 185.5 ± 21.1 |
| | 796-37-31 | $GI_{50}$ | 24 hr | | | | |
| | | | 48 hr | | | | >750 |
| | | | 72 hr | 50-100 | | | 185.5 ± 21.1 |
| | | $IC_{50}$ | 24 hr | | | | |
| | | | 48 hr | | | >750 | |
| | | | 72 hr | 250-500 | | >750 | |
| | 796-37-35 | $GI_{50}$ | 24 hr | | | | |
| | | | 48 hr | | | >750 | |
| | | | 72 hr | 10-50 | | 100-250 | |
| | | $IC_{50}$ | 24 hr | | | | |
| | | | 48 hr | >750 | 500-750 | | >750 |
| | | | 72 hr | 250-500 | 500-750 | 500-750 | 250-500 |
| | | $GI_{50}$ | 24 hr | | | | |
| | | | 48 hr | 10-50 | ≈500 | | 100-250 |
| | | | 72 hr | <10 | 250-500 | 10-50 | 50-100 |
| | | | (µg/ml) | | <100 | 100-500 | >500 |

Anti Proliferation Activity of HXLS Extracts on Six Human Cancer Cells

To evaluate the anti-proliferation activity of HXLS extracts on the six current highest worldwide prevalence cancers, differentiated lung (A549), stomach (AGS), colorectal (HT-29), breast (MCF-7), prostate (PC-3), and cervical (HeLa) cancer cell lines were incubated with the extract samples for 24, 48 or 72 hours. The cell viability was determining with MTT assays. The anti-proliferation activity was expressed in terms of IC50 and GI50 as defined previously.

Seven extracts were selected from the ten extracts exhibiting potent anti-HCC activities mentioned in Example 2 for the study, which are test articles numbered 796-37-03, 796-37-06, 796-37-11, 796-37-16, 796-37-29, 796-37-(16+29), and 796-37-35. Table 7 shows that from high to low potency order, test articles numbered 796-37-(16+29), 796-37-16, 796-37-06, and 796-37-29 exhibited potent inhibitory activities on the growth of cells of the six cancer cell lines mentioned above. It was interesting to find that among the seven test articles the ones prepared from single ingredient raw materials, i.e., test articles numbered 796-37-16, an HXLS-G extract and 796-37-29, an HXLS-S extract, all exhibited good anti-cancer activities, while among the ones prepared from more than one ingredient raw materials, only the test article numbered 796-37-06, an HXLS-GSP extract, and 796-37-(16+29), a mixture of HXLS-G and HXLS-S extracts, exhibited fair anti-cancer activities and the rest exhibited poor anti-cancer activities.

All the test articles exhibiting anti-cancer activities mentioned above have selective inhibitory activities to the six human cancer cell lines. The test article numbered 796-37-06 was effective on A549 (lung), HT-29 (colorectal), MCF-7 (breast), PC-3 (prostate), and HeLa (cervical)) but ineffective to AGS (stomach), while test articles numbered 796-37-(16+29) and 796-37-29 were effective on A549 (lung), HT-29 (colorectal), MCF-7 (breast), PC-3 (prostate), and AGS (stomach)) but ineffective to HT-29 (cervical). Only the test article numbered 796-37-16 was effective on all six human cancer cell lines.

Conclusions

The in vitro cellular assay result demonstrated positive pharmacological activities of the thirty one (31) extracts of the formula against four cell based pharmacological action model platforms, namely, HBV antigen expression, inflammation cytokine secretion, proliferation of four liver cancer cell line cells, and proliferation of cancer cell line cells of six cancers including lung, stomach, prostate, colorectal, cervical, and breast cancer. Specifically, results showed that, among the fifty (50) extracts, samples 796-37-19 and 796-37-23 exhibited better anti-HBV activity; samples 796-37-06 and 796-37-11 exhibited better anti-TNF-α activity; samples 796-37-35, 796-37-(16+29), 796-37-10 and 796-37-06 exhibited better inhibitory activity on liver cancer cell proliferation; and samples 796-37-(16+29), 796-37-16, and 796-37-06 exhibited better inhibitory activity on cell proliferation of the above-mentioned six cancer cell lines.

TABLE 7

Anti-proliferation effect of HXLS extracts on six most frequent types of human cancer.

| Material | Test articles | µg/ml | cell time | A549 Lung | AGS Stomach | HeLa Cervical | HT-29 Colorectal | MCF-7 Breast | PC-3 Prostate |
|---|---|---|---|---|---|---|---|---|---|
| HXLS-GSP | 796-37-03 | $IC_{50}$ | 24 hr | 153 ± 11 | 197 ± 5 | 276 ± 4 | 144 ± 11 | 191 ± 20 | 191 ± 8 |
| | | | 48 hr | 217 ± 21 | 445 ± 47 | 250-500 | 310 ± 41 | ≈250 | ≈750 |
| | | | 72 hr | 325 ± 35 | 249 ± 10 | >750 | ≈250 | >750 | >750 |
| | | $GI_{50}$ | 24 hr | 153 ± 11 | 197 ± 5 | 276 ± 4 | 144 ± 11 | 191 ± 20 | 191 ± 8 |
| | | | 48 hr | 217 ± 21 | 445 ± 47 | 100-250 | 41 ± 8 | 50-100 | 100-250 |
| | | | 72 hr | 325 ± 35 | 249 ± 10 | >750 | ≈250 | 252 ± 44 | 389 ± 71 |

TABLE 7-continued

Anti-proliferation effect of HXLS extracts on six most frequent types of human cancer.

| Material | Test articles | | μg/ml | cell time | A549 Lung | AGS Stomach | HeLa Cervical | HT-29 Colorectal | MCF-7 Breast | PC-3 Prostate |
|---|---|---|---|---|---|---|---|---|---|---|
| | 796-37-06 | IC$_{50}$ | | 24 hr | ≈100 | 113 ± 1 | ≈250 | 59 ± 14 | ≈250 | ≈250 |
| | | | | 48 hr | 50-100 | 203 ± 25 | 100-250 | 66 ± 2 | 100-250 | 250-500 |
| | | | | 72 hr | 79 ± 11 | ≈500 | 244 ± 14 | 94 ± 9 | ≈250 | ≈750 |
| | | GI$_{50}$ | | 24 hr | 10-50 | 113 ± 1 | 50-100 | 59 ± 14 | 50-100 | ≈10 |
| | | | | 48 hr | 10-50 | 203 ± 25 | 10-50 | 66 ± 2 | 50-100 | ≈50 |
| | | | | 72 hr | 79 ± 11 | 250-500 | 244 ± 14 | 94 ± 9 | ≈50 | 284 ± 43 |
| | 796-37-11 | IC$_{50}$ | | 24 hr | 352 ± 38 | ≈250 | ≈250 | 313 ± 70 | >750 | 187 ± 20 |
| | | | | 48 hr | 356 ± 24 | 100-250 | 124 ± 17 | 251 ± 30 | ≈250 | >750 |
| | | | | 72 hr | 250-500 | 139 ± 10 | 100-250 | 250-500 | ≈250 | >750 |
| | | GI$_{50}$ | | 24 hr | 352 ± 38 | 100-250 | 100-250 | 313 ± 70 | 100-250 | 187 ± 20 |
| | | | | 48 hr | 356 ± 24 | 100-250 | 124 ± 17 | 251 ± 30 | 100-250 | 67 ± 2 |
| | | | | 72 hr | 50-100 | 139 ± 10 | 50-100 | ≈250 | 50-100 | 50-100 |
| HSLS-G + S + P | 796-37-35 | IC$_{50}$ | | 24 hr | >750 | ≈500 | >750 | 500-750 | 278 ± 29 | ≈750 |
| | | | | 48 hr | >750 | 250-500 | ≈500 | 100-250 | 100-250 | ≈50 |
| | | | | 72 hr | >750 | 319 ± 54 | 132 ± 24 | ≈100 | 178 ± 31 | >750 |
| | | GI$_{50}$ | | 24 hr | 10-50 | ≈100 | 250-500 | 250-500 | 278 ± 29 | 100-250 |
| | | | | 48 hr | 47 ± 9 | 250-500 | 100-250 | 100-250 | 100-250 | 10 ± 2 |
| | | | | 72 hr | 50-100 | 319 ± 54 | 132 ± 24 | ≈100 | 178 ± 31 | 100-250 |
| | | | (μ/ml) | | <100 | 100-500 | >500 | | | |

Example 3

EL4 Cell Activity

The cell assay is to explore the test articles' activity on the immune response. IL-4 is the trophic factor for the T helper cell. The effect on IL-4 activity will be carried out for all test articles, and the IC50 of each sample is calculated to show the half inhibitory concentration of the cellular secretion of IL-4. Each sample is incubated with mouse lymphoma EL-4 cells for 2 hours, and the cells are stimulated with PMA and A23187 overnight. The cell viability is determined by MTT assays, and the secretion of IL-4 is measured with ELISA. The higher inhibitory activity was obtained in samples of 796-37-11, 796-37-11', 796-37-06, 796-37-09, and 796-37-43.

TABLE 8

Effect of immune system response for HXLS extracts

| Test Articles | IC50 |
|---|---|
| 796-37-11 | 49 ± 1 |
| 796-37-11' | 66 ± 4 |
| 796-37-06 | 96 ± 1 |

Example 4

In Vivo Pharmacological Study of the HXLS Formula Extracts

Having determined the efficacy of the HXLS formula extracts in the in vitro studies listed above, the following experiments detail the compositions' efficacy in several in vivo models of chronic disease.

Acute Hepatitis

Thioacetamide (TAA): Effect on acute hepatitis induced by oxidative stress. TAA in rats is evaluated by the oral administration of different test articles for 1 hour to 7 days before TAA injection. TAA injection is at a single dose 300 mg/kg; solved in saline; intraperitoneal (hereinafter as "i.p.") volume: 5 ml/kg (60 mg/ml). Blood drawn at 300 μl/time will be performed at day 1 (0 hour), day 8 (24 hour) and day 9 (48 hour). The liver enzymes ALT and AST in the blood are measured. The animal selected for the test are 8 weeks old male Wistar rats, and the vehicle are provided with 0.5% CMC or 5% corn starch in 0.5% CMC while test articles 796-37-03, 796-37-06, and 796-37-11 are provided at 500 mg/kg. 8 rats will be used for each extract samples. Higher inhibitory activity was observed in both AST and ALT for test article 796-37-03.

TABLE 9

Effect of TAA in animal for HXLS extracts

| | AST (U/L) | | | ALT (U/L) | | |
|---|---|---|---|---|---|---|
| TAA | 0 hr | 24 hr | 48 hr | 0 hr | 24 hr | 48 hr |
| Vehicle | 102.8 | 3918.8 | 2745.7 | 77.1 | 748.8 | 1378.8 |
| 500 mg/kg 796-37-03 | 101.4 | 3293.8 | 1996.3 | 70.5 | 554.3 | 920.0 |
| 500 mg/kg 796-37-06 | 101.7 | 3481.4 | 2451.4 | 73.1 | 745.7 | 1046.7 |
| 500 mg/kg 796-37-11 | 95.8 | 3112.5 | 2180.0 | 78.3 | 742.5 | 986.3 |

Lipopolysaccharide (LPS)/TNF receptor superfamily, member 6 (FAS):

Effect on acute hepatitis induced by apoptosis agent i.e. LPS/FAS in mice is evaluated by the oral administration of different test articles for 1 hour to 7 days before LPS/FAS injection. The liver histology is examined for the tissue damage.

The animals selected for the test are 10 weeks old male, Balb/c mice, and each test articles were provided with 10 mice. The vehicle are provided with 0.5% CMC or 5% corn starch in 0.5% CMC while test articles 796-37-03, 796-37-06, and 796-37-11 are provided at 500 mg/kg. On day 0, mice were injected in i.p. volume 1 mg/mouse heat-killed P. acnes (Propionibacterium acnes, BCRC Number: 16146); on day 7, 1 hour after different test articles were provided, mice were injected in i.p. volume 2 μg/mouse LPS (lipopolysaccharide); then 1 mg/mouse heat-killed P. acnes solved in 100 μl PBS and 2 μg/mouse LPS solved in 100 μl PBS; continue to provide test articles for 7 days, and 1 hour after the last dose, i.p. of LPS; now observe mice health status and survival rate. The higher protection activity on LPS-induced fulminant hepatitis model was obtained in test article 796-37-06.

TABLE 10

Effect of LPS-induced fulminate model in animal for HXLS extracts

| LPS-induced fulminant | 1 hr | 12 hr | 24 hr | 36 hr | 48 hr | 60 hr | 72 hr |
|---|---|---|---|---|---|---|---|
| Vehicle | 100% | 90% | 80% | 10% | 10% | 10% | 10% |
| 500 mg/kg 796-37-03 | 100% | 90% | 90% | 0% | 0% | 0% | 0% |
| 500 mg/kg 796-37-06 | 100% | 100% | 100% | 40% | 30% | 30% | 30% |
| 500 mg/kg 796-37-11 | 100% | 90% | 80% | 40% | 20% | 0% | 0% |

The animals selected for the test are 9 weeks old male, Balb/c mice, and each test articles were provided with 10 mice. The vehicle are provided with 0.5% CMC or 5% corn starch in 0.5% CMC while test articles 796-37-03, 796-37-06, and 796-37-11 are provided at 500 mg/kg. Repeat the same test as LPS and replaced the LPS dosage with Fas, anti-Fas/APO-1 (BD Pharmingen554254), clone: Jo2, anti-Fas Ab dosage: 10 µg/mouse, solved in saline; ip volume: 100 µl/mouse (0.1 m/µl); and observe mice health status and survival rate as LPS. The higher protection activity on Fas-induced fulminant hepatitis model was obtained in test article 796-37-06 and 796-37-011.

TABLE 11

Effect of Fas-induced fulminate model in animal for HXLS extracts

| Fas-induced fulminant | 0 hr | 1 hr | 2 hr | 3 hr | 4 hr | 5 hr | 6 hr | 7 hr | 8 hr | 9 hr | 22 hr |
|---|---|---|---|---|---|---|---|---|---|---|---|
| Vehicle | 100% | 100% | 100% | 100% | 100% | 40% | 20% | 10% | 0% | 0% | 0% |
| 500 mg/kg 796-37-03 | 100% | 100% | 100% | 100% | 100% | 80% | 50% | 40% | 30% | 20% | 10% |
| 500 mg/kg 796-37-06 | 100% | 100% | 100% | 100% | 100% | 90% | 90% | 60% | 40% | 40% | 20% |
| 500 mg/kg 796-37-11 | 100% | 100% | 100% | 100% | 100% | 80% | 60% | 50% | 40% | 40% | 20% |

Liver Cancer

Effect on liver cancer induced by chemical agent i.e. DEN in mice or in rats is evaluated by the oral administration of different extracts on the day of DEN injection throughout the eight weeks study period. The animals selected for the test are 8 weeks old C57BL6 mice from NLAC, and each test articles were provided with 12 mice. The vehicle are provided with 0.5% CMC or 5% corn starch in 0.5% CMC while test articles 796-37-03, 796-37-06, and 796-37-11 are provided daily at 500 mg/kg for eight weeks. On week 0 to week 3, mice were injected with i.p. DEN 75 mg/kg., solved in saline, i.p. volume: 10 ml/kg, once/week; on week 4 to week 5, mice were injected with i.p. DEN 100 mg/kg. once/week; and blood collected at week 0, 2, 4, 6, 8 by submandibular Bleed on the next day after i.p. DEN with liver enzyme ALT in the blood are measured. The higher protection activity was obtained in test article 796-37-06.

TABLE 12

Effect of chemical induced liver cancer in animal for HXLS extracts

| Liver Cancer | W0 | W2 | W4 | W6 | W8 |
|---|---|---|---|---|---|
| Vehicle | 50.9 | 117.3 | 150.6 | 402.3 | 445.9 |
| 500 mg/kg 796-37-03 | 55.5 | 124.7 | 150.9 | 562.0 | 493.3 |
| 500 mg/kg 796-37-06 | 46.5 | 89.0 | 118.8 | 362.3 | *314.2* |
| 500 mg/kg 796-37-11 | 49.3 | 129.1 | 145.8 | 466.0 | 331.6 |

Immune System Response

Effect on the specific immune response to allergen in mice: i.e. The effect on IL-4 activity will be carried out for different test articles. The immune response of a specific allergen immunized mice is evaluated with the oral administration of 3 different extracts. The animals selected for the test are 5 weeks old BALB/c mouse, and each test articles were provided with 5 mice. The mouse were provided with Immunization on day 0, i.p. inject OVA 100 µg/25 g mouse with aluminum to elicit the immune response to OVA; and booster were provided on day 14, i.p. inject OVA 50 m/25 g mouse with aluminum to elicit the secondary immune response; and bleeding were performed where mice blood were taken at various time points (Day 0, 14, 21, 28) to obtain the time course of the antibody production. Observation were made on Total-IgG, Total-IgE, OVA-specific IgG and OVA-specific IgE in serum; Splenocyte proliferation with stimulation of mitogen and OVA; Splenocyte cytokines secretion (SSP) with stimulation of mitogen and OVA (cytokine) for IL-2, IL-4, IL-10, IFN-γ; and Phagocytic activity of blood cells. The higher inhibitory activity was obtained in samples of 796-37-03.'

TABLE 13

Effect of immune system response, Total IgG, in animals for HXLS extracts

| Test Articles | SD0 | SD0 | SD21 | SD28 |
|---|---|---|---|---|
| Vehicle | 216 | 1322 | 1275 | 1071 |
| 796-37-03' | 243 | 793 | 1341 | 903 |
| 796-37-06 | 69 | 555 | 1219 | 1117 |
| 796-37-11' | 114 | 1054 | 1131 | 1126 |

TABLE 14

Effect of immune system response in animals for HXLS extracts

| Test Articles | Ova IgG | OVA IgE | Con-A SSP | OVA SSP |
|---|---|---|---|---|
| Vehicle | 0.514 | 0.277 | 1.75 | 0.6 |
| 796-37-03' | 0.338 | 0.133 | 1.58 | 0.39 |
| 796-37-06 | 0.414 | 0.195 | 1.26 | 0.79 |
| 796-37-11' | 0.258 | 0.13 | 1.61 | 0.75 |

The examples, which are intended to be purely exemplary of the invention and should therefore not be considered to limit the invention in any way, also describe and detail aspects and embodiments of the invention discussed above. The foregoing examples and detailed description are offered by way of illustration and not by way of limitation. All publications, patent applications, and patents cited in this specification are herein incorporated by reference as if each individual publication, patent application, or patent were specifically and individually indicated to be incorporated by reference. In particular, all publications cited herein are expressly incorporated herein by reference for the purpose of describing and disclosing compositions and methodologies which might be used in connection with the invention. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

REFERENCES

United States Patent Application 20090130138. Antiviral and antibacterial activity from medicinal mushrooms, by Stamets; Paul Edward May 21, 2009

United States Patent Application 20090118364. Novel diterpenes from the fruiting body of antrodia camphorata and pharmaceutical compositions thereof, by Lai; Min-Nan; et al. May 7, 2009

United States Patent Application 20070041993. Compositions and methods for symptomatic relief, by Holcomb-Halstead; Terri Lee; et al. Feb. 22, 2007

United States Patent Application 20060110479. Natural composition for curing hepatitis-B, methods for making the same and pharmaceutical formulations thereof, by Mitra; Shankar Kumar; et al. May 25, 2006

WO/2006/015556. A ANTIVIRAL COMBINATION AND THEREOF MANUFACTURE, by TIAN, Shengxun; Feb. 16, 2006

United States Patent Application 20050129780. Relief of aids symptoms, by Holcomb-Halstead, Terri Lee; et al. Jun. 16, 2005

United States Patent Application 20030113297. Liver-caring medicine containing antrodia camphorata, by Chen, Jinn-Chu; et al. Jun. 19, 2003

U.S. Pat. No. 7,456,225. Liver protection compounds of the cyclohexenone type from Antrodia camphorata, by Liu, et al. Nov. 25, 2008

WO/2002/032444. NOVEL MEDICINAL HERBAL COMPOSITION FOR TREATING LIVER DISEASES AND HIV, by WU, Tzu-Sheng; Apr. 25, 2002

WO/1997/002831. HERBAL COMPOSITIONS FOR HEPATIC DISORDERS, by YANG, Yi, Fan; Jan. 30, 1997

What is claimed is:

1. A composition consisting essentially of:
   a *Panax ginseng* extract or a *Panax quinquefolia* extract;
   a *Ganoderma lucidum* extract;
   a *Saussurea involucrata* extract; and
   optionally, at least one pharmaceutical excipient;
   wherein the extracts are in amounts effective to inhibit hepatitis B virus, inflammation, and/or cancer cell proliferation,
   wherein the extracts are prepared by extracting raw materials of *Panax ginseng* or *Panax quinquefolia*, *Ganoderma lucidum*, and *Saussurea involucrata* in a ratio of about 1:1:1,
   wherein the extracts are extracted in an extraction solvent separately or in a mixture, with reflux or at 60° C., and
   wherein the extraction solvent is selected from the group consisting of water, ethanol, and a combination of water and ethanol.

2. The composition of claim 1, consisting of the extracts and optionally at least one pharmaceutical excipient.

3. The composition of claim 1, wherein the composition is in a dosage form selected from the group consisting of a solution, a suspension, a liquid, a powder, a granule, an injection, a tablet, a capsule, and a pill.

4. The composition of claim 1, wherein the extracts are prepared by a process comprising:
   mixing the raw materials of *Panax ginseng* or *Panax quinquefolia*, *Ganoderma lucidum*, and *Saussurea involucrata*; and
   extracting the mixture in water with reflux.

5. The composition of claim 1, wherein the extracts are prepared by a process comprising:
   mixing the raw materials of *Panax ginseng* or *Panax quinquefolia*, *Ganoderma lucidum*, and *Saussurea involucrata*; and
   extracting the mixture in 40% ethanol at 60° C.

6. The composition of claim 1, wherein the extracts are prepared by a process comprising:
   mixing the raw materials of *Panax ginseng* or *Panax quinquefolia*, *Ganoderma lucidum*, and *Saussurea involucrata*; and
   extracting the mixture in 95% ethanol with reflux.

7. The composition of claim 1, wherein the extracts are prepared by a process comprising:
   mixing the raw materials of *Panax ginseng* or *Panax quinquefolia*, *Ganoderma lucidum*, and *Saussurea involucrata*; and
   extracting the mixture in 95% ethanol at 60° C.

8. The composition of claim 1, wherein the extracts are prepared by a process comprising:
   separately extracting the raw materials of *Panax ginseng* or *Panax quinquefolia*, *Ganoderma lucidum*, and *Saussurea involucrata* in water with reflux; and
   combining the extracts.

9. The composition of claim 1, wherein the extracts are prepared by a process comprising:
   separately extracting the raw materials of *Panax ginseng* or *Panax quinquefolia*, *Ganoderma lucidum*, and *Saussurea involucrata* in 95% ethanol with reflux; and
   combining the extracts.

* * * * *